(12) United States Patent
George et al.

(10) Patent No.: US 10,820,899 B2
(45) Date of Patent: Nov. 3, 2020

(54) ARTHROSCOPIC KNOT PUSHER AND SUTURE CUTTER

(71) Applicant: Ceterix Orthopaedics, Inc., Fremont, CA (US)

(72) Inventors: William R. George, Santa Cruz, CA (US); Michael J. Hendricksen, Redwood City, CA (US); Chad R. Yolland, San Francisco, CA (US); Michael Murillo, Menlo Park, CA (US)

(73) Assignee: Ceterix Orthopaedics, Inc., Fremont, CA (US)

(*) Notice: Subject to any disclaimer, the term of this patent is extended or adjusted under 35 U.S.C. 154(b) by 135 days.

(21) Appl. No.: 16/208,526

(22) Filed: Dec. 3, 2018

(65) Prior Publication Data
US 2019/0099176 A1 Apr. 4, 2019

Related U.S. Application Data

(63) Continuation of application No. 15/145,627, filed on May 3, 2016, now Pat. No. 10,143,464, which is a continuation-in-part of application No. 14/608,057, filed on Jan. 28, 2015, now Pat. No. 9,332,980, which is a continuation of application No. 14/494,561, filed on Sep. 23, 2014, now Pat. No. 9,247,935.

(60) Provisional application No. 61/881,319, filed on Sep. 23, 2013.

(51) Int. Cl.
*A61B 17/04* (2006.01)
(52) U.S. Cl.
CPC ...... *A61B 17/0469* (2013.01); *A61B 17/0467* (2013.01); *A61B 2017/0474* (2013.01)

(58) Field of Classification Search
CPC .......... A61B 17/00234; A61B 17/0467; A61B 17/0469; A61B 2017/0474
See application file for complete search history.

(56) References Cited

U.S. PATENT DOCUMENTS

| | | |
|---|---|---|
| 1,037,864 A | 9/1912 | Carlson et al. |
| 2,738,790 A | 3/1956 | Todt, Sr. et al. |
| 2,748,773 A | 6/1956 | Vacheresse, Jr. |
| 3,470,875 A | 10/1969 | Johnson |
| 3,580,256 A | 5/1971 | Wilkinson et al. |
| 3,807,407 A | 4/1974 | Schweizer |

(Continued)

FOREIGN PATENT DOCUMENTS

| | | |
|---|---|---|
| CN | 201263696 Y | 7/2009 |
| CN | 101961256 A | 2/2011 |

(Continued)

OTHER PUBLICATIONS

French Patent Opinion and Search Report FR1753894.

(Continued)

*Primary Examiner* — Jocelin C Tanner
(74) *Attorney, Agent, or Firm* — Norman F. Hainer, Jr.

(57) ABSTRACT

Knot pushers and suture cutter apparatuses to be used arthroscopically, for example, in an arthroscopic knee surgery may be operated with a single control to both lock the suture within the distal end of the apparatus and cut the suture once the knot has been pushed to the appropriate location. The apparatus may include a safety lock preventing deployment of the cutter until the safety lock (e.g., cutter release) has been released.

19 Claims, 25 Drawing Sheets

(56) References Cited

U.S. PATENT DOCUMENTS

| | | |
|---|---|---|
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,553,543 A | 11/1985 | Amarasinghe |
| 4,605,002 A | 8/1986 | Rebuffat |
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,059,206 A | 10/1991 | Winters |
| 5,112,344 A | 5/1992 | Petros |
| 5,129,912 A | 7/1992 | Noda et al. |
| 5,139,520 A | 8/1992 | Rosenberg |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,320,633 A | 6/1994 | Allen et al. |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,383,877 A | 1/1995 | Clarke |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,431,669 A | 7/1995 | Thompson et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,756 A | 4/1996 | Hasson |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,748 A | 5/1997 | Beck et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,797,958 A | 8/1998 | Yoon |
| 5,800,445 A | 9/1998 | Ratcliff et al. |
| 5,814,054 A | 9/1998 | Kortenbach et al. |
| 5,814,069 A | 9/1998 | Schulze et al. |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,910,148 A | 6/1999 | Reimels et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 5,997,554 A | 12/1999 | Thompson |
| 6,039,753 A | 3/2000 | Meislin |
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,099,568 A | 8/2000 | Simonian et al. |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |
| 6,159,224 A | 12/2000 | Yoon |
| 6,190,396 B1 | 2/2001 | Whitin et al. |
| 6,221,085 B1 | 4/2001 | Djurovic |
| 6,231,606 B1 | 5/2001 | Graf et al. |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,355,050 B1 | 3/2002 | Andreas et al. |
| 6,368,334 B1 | 4/2002 | Sauer |
| 6,368,343 B1 | 4/2002 | Bonutti et al. |
| 6,443,963 B1 | 9/2002 | Baldwin et al. |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |

(56) References Cited

U.S. PATENT DOCUMENTS

| | | | |
|---|---|---|---|
| 6,641,592 B1 | 11/2003 | Sauer et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,833,005 B1 | 12/2004 | Mantas |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,972,027 B2 | 12/2005 | Fallin et al. |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,153,312 B1 | 12/2006 | Torrie et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,481,826 B2 | 1/2009 | Cichocki |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,717,927 B2 * | 5/2010 | Hahn ............... A61B 17/0469 606/148 |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,879,055 B1 | 2/2011 | Stone et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,972,344 B2 | 7/2011 | Murray et al. |
| 8,211,123 B2 | 7/2012 | Gross et al. |
| 8,298,230 B2 | 10/2012 | Sutter et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 8,465,505 B2 | 6/2013 | Murillo et al. |
| 8,500,809 B2 | 8/2013 | Saliman |
| 8,562,631 B2 | 10/2013 | Saliman |
| 8,603,125 B2 | 12/2013 | Stone et al. |
| 8,632,563 B2 | 1/2014 | Nagase et al. |
| 8,647,354 B2 | 2/2014 | Domingo |
| 8,663,253 B2 | 3/2014 | Saliman |
| 8,702,731 B2 | 4/2014 | Saliman |
| 8,808,299 B2 | 8/2014 | Saliman et al. |
| 8,821,518 B2 | 9/2014 | Saliman |
| 8,888,848 B2 | 11/2014 | Saliman et al. |
| 8,911,456 B2 | 12/2014 | McCutcheon et al. |
| 8,920,441 B2 | 12/2014 | Saliman et al. |
| 9,011,454 B2 | 4/2015 | Hendrickson et al. |
| 9,211,119 B2 | 12/2015 | Hendrickson et al. |
| 9,247,934 B2 | 2/2016 | Murillo et al. |
| 9,247,935 B2 | 2/2016 | George et al. |
| 9,314,234 B2 | 4/2016 | Hirotsuka et al. |
| 9,332,980 B2 | 5/2016 | George et al. |
| 9,492,162 B2 | 11/2016 | Murillo et al. |
| 9,700,299 B2 | 7/2017 | Saliman et al. |
| 9,848,868 B2 | 12/2017 | Saliman |
| 9,861,354 B2 | 1/2018 | Saliman et al. |
| 9,913,638 B2 | 3/2018 | Saliman et al. |
| 10,004,492 B2 | 6/2018 | Hendricksen et al. |
| 10,143,464 B2 | 12/2018 | George et al. |
| 2001/0041938 A1 | 11/2001 | Hein |
| 2002/0169477 A1 | 11/2002 | Demopulos et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0078617 A1 | 4/2003 | Schwartz et al. |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0117014 A1 | 6/2004 | Bryant |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0043746 A1 | 2/2005 | Pollak et al. |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0178680 A1 | 8/2006 | Beverly et al. |
| 2006/0282098 A1 | 12/2006 | Shelton et al. |
| 2006/0293700 A1 * | 12/2006 | Dana ............... A61B 17/0485 606/148 |
| 2007/0032799 A1 | 2/2007 | Pantages et al. |
| 2007/0038230 A1 | 2/2007 | Stone et al. |
| 2007/0156174 A1 | 7/2007 | Kaiser et al. |
| 2007/0185532 A1 | 8/2007 | Stone et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0086147 A1 | 4/2008 | Knapp |
| 2008/0091219 A1 | 4/2008 | Marshall et al. |
| 2008/0097482 A1 | 4/2008 | Bain et al. |
| 2008/0097489 A1 | 4/2008 | Goldfarb et al. |
| 2008/0140091 A1 | 6/2008 | DeDeyne et al. |
| 2008/0140094 A1 | 6/2008 | Schwartz et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0275553 A1 | 11/2008 | Wolf et al. |
| 2008/0294256 A1 | 11/2008 | Hagan et al. |
| 2009/0012520 A1 | 1/2009 | Hixson et al. |
| 2009/0012538 A1 | 1/2009 | Saliman |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0112232 A1 | 4/2009 | Crainich et al. |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |

(56) References Cited

U.S. PATENT DOCUMENTS

| | | |
|---|---|---|
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2011/0022061 A1 | 1/2011 | Orphanos et al. |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0071563 A1 | 3/2011 | Magliani |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0251626 A1 | 10/2011 | Wyman et al. |
| 2011/0270306 A1 | 11/2011 | Denham et al. |
| 2012/0101524 A1 | 4/2012 | Bennett |
| 2012/0303046 A1 | 11/2012 | Stone et al. |
| 2013/0072948 A1 | 3/2013 | States, III et al. |
| 2013/0085512 A1 | 4/2013 | Wyman et al. |
| 2013/0253536 A1 | 9/2013 | Harris et al. |
| 2014/0188136 A1 | 7/2014 | Cournoyer et al. |
| 2014/0222034 A1 | 8/2014 | Saliman |
| 2015/0034694 A1 | 2/2015 | Cappola |
| 2015/0073442 A1 | 3/2015 | Saliman et al. |
| 2015/0157317 A1 | 6/2015 | Bagaoisan et al. |
| 2015/0173742 A1 | 6/2015 | Palese et al. |
| 2015/0173743 A1 | 6/2015 | Palese et al. |
| 2015/0209029 A1 | 7/2015 | Hendricksen et al. |
| 2015/0257756 A1 | 9/2015 | Sauer |
| 2015/0297215 A1 | 10/2015 | Hendricksen et al. |
| 2015/0313589 A1 | 11/2015 | Hendricksen et al. |
| 2016/0220244 A1 | 8/2016 | Murillo et al. |
| 2016/0302789 A1 | 10/2016 | Hirotsuka et al. |
| 2017/0020512 A1 | 1/2017 | Murillo et al. |
| 2017/0027558 A1 | 2/2017 | Murillo et al. |
| 2017/0119372 A1 | 5/2017 | Peter et al. |
| 2018/0116651 A1 | 5/2018 | Saliman |
| 2018/0125479 A1 | 5/2018 | Saliman et al. |
| 2018/0199931 A1 | 7/2018 | Saliman et al. |
| 2018/0303476 A1 | 10/2018 | Murillo et al. |

FOREIGN PATENT DOCUMENTS

| | | |
|---|---|---|
| CN | 103298503 A | 9/2013 |
| CN | 103717149 A | 4/2014 |
| EP | 0647431 A2 | 4/1995 |
| EP | 2030575 A1 | 3/2009 |
| EP | 2184015 A2 | 5/2010 |
| EP | 2081481 B1 | 11/2015 |
| JP | 3032847 U | 3/1991 |
| JP | 2009138029 A | 6/2009 |
| JP | 2009538190 A | 11/2009 |
| SU | 376089 A | 4/1973 |
| SU | 728848 A1 | 4/1980 |
| SU | 1725847 A1 | 4/1992 |
| WO | WO92/05828 A1 | 4/1992 |
| WO | WO95/13021 A1 | 5/1995 |
| WO | WO98/11825 A1 | 3/1998 |
| WO | WO98/31288 A1 | 7/1998 |
| WO | WO99/34744 A1 | 7/1999 |
| WO | WO99/42036 A1 | 8/1999 |
| WO | WO99/47050 A2 | 9/1999 |
| WO | WO01/56478 A1 | 8/2001 |
| WO | WO02/07607 A1 | 1/2002 |
| WO | WO02/096296 A1 | 12/2002 |
| WO | WO03/077771 A1 | 9/2003 |
| WO | WO2006/001040 A1 | 1/2006 |
| WO | WO2006/040562 A1 | 4/2006 |
| WO | WO2010/141695 A1 | 12/2010 |
| WO | WO2011/057245 A2 | 5/2011 |

OTHER PUBLICATIONS

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05 &p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Ceterix; Novocut suture manager; retrieved from the internet (https://web.archive.org/web/20150314071511/http://www.ceterix.com:80/im-a-physician/products/) on Oct. 11, 2017; 1 page; Mar. 12, 2015.

Ceterix; Novocut suture manager; retrieved from the internet (https://www.youtube.com/watch?v=6txqBJxvnuA) on Oct. 11, 2017; 1 page; Mar. 5, 2015.

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2 pgs.

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

Dictionary.com; Adjacent (definition); 5 pgs.; retrieved from the internet (http://www.dictionary.com/browse/adjacent) on Apr. 5, 2016.

Duerig, T. et al., "An overview of nitinol medical applications" Materials Science and Engineering A273-275, pp. 149-160; May 1999.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

MEDSFERA; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).

(56) References Cited

OTHER PUBLICATIONS

Rimmer et al.; Failure Strength of Different Meniscal Suturing Techniques; Arthroscopy: The Journal of Arthroscopic and Related Surgery; vol. 11; No. 2; pp. 146-150; Apr. 1995.

Schneeberger, et al; "Mechanical Strength of Arthroscopic Rotator Cuff Repair Techniques: An in Vitro Study," J Bone Joint Surg Am., Dec. 2002; 84:2152-2160.

Smith&Nephew; Fast-Fix Meniscal Repair System (product webpage); 4 pgs.; downloaded Nov. 21, 2011 (http://endo.smith-nephew.com/fr/node.asp?Nodeld=3562).

Strobel; Manual of Arthroscopic Surgery (1st Edition); Springer Verlag, Hiedelberg ©2002; pp. 127-129; Dec. 15, 2001.

USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.

USS SportsMedicine ArthroSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

\* cited by examiner

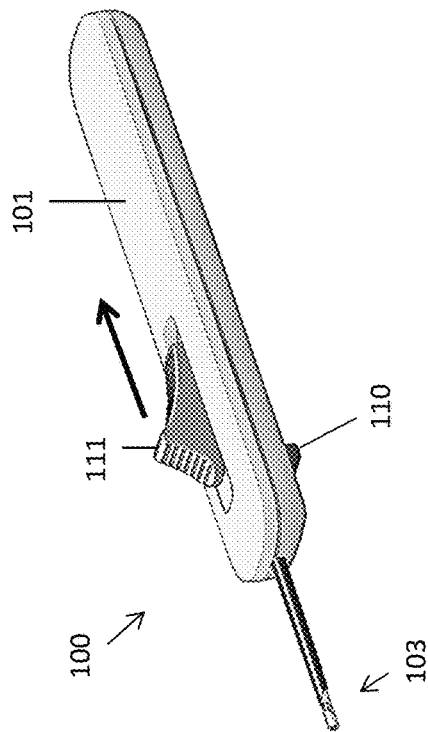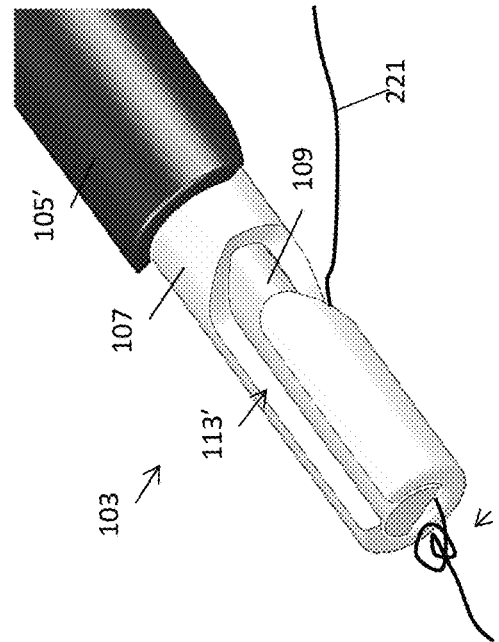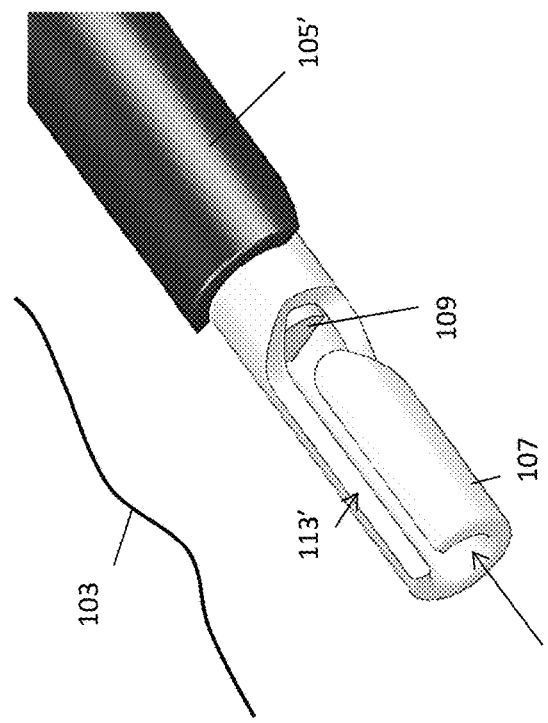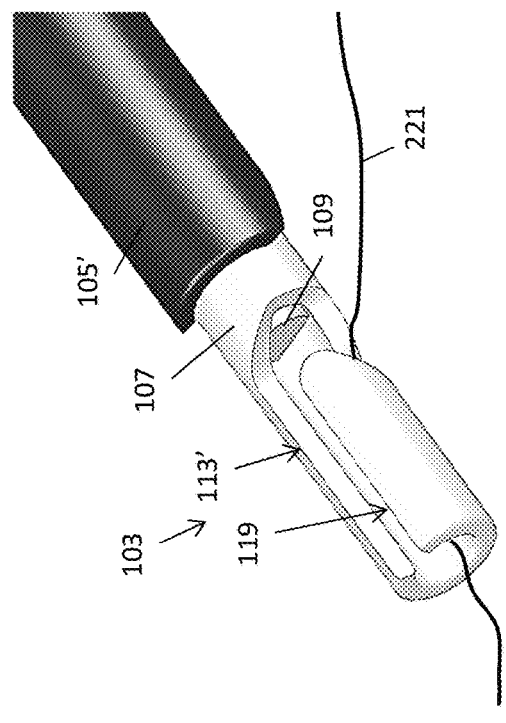
FIG. 3A
FIG. 3B
FIG. 4
FIG. 5A

ARTHROSCOPIC KNOT PUSHER AND SUTURE CUTTER

CROSS REFERENCE TO RELATED APPLICATIONS

This patent application is a continuation of U.S. patent application Ser. No. 15/145,627, filed May 3, 2016, titled "ARTHROSCOPIC KNOT PUSHER AND SUTURE CUTTER," now U.S. Pat. No. 10,143,464, which is a continuation-in-part of U.S. patent application Ser. No. 14/608,057, filed Jan. 28, 2015, titled "ARTHROSCOPIC KNOT PUSHER AND SUTURE CUTTER," now U.S. Pat. No. 9,332,980, which is a continuation of U.S. patent application Ser. No. 14/494,561, filed on Sep. 23, 2014, titled "ARTHROSCOPIC KNOT PUSHER AND SUTURE CUTTER," now U.S. Pat. No. 9,247,935, which claims priority to U.S. Provisional Patent Application No. 61/881,319, filed on Sep. 23, 2013, and titled "ARTHROSCOPIC KNOT PUSHER AND SUTURE CUTTER," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates to suturing techniques, devices and methods, and in particular to knot pusher and suture cutter apparatuses and method of use them during surgery, such as arthroscopic surgery.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments have been developed to assist in accessing and treating internal body regions, and to generally assist a physician in repairing tissue. Although many such devices are available for endoscopic, arthroscopic, and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

Further, when performing surgery, such as arthroscopic surgery, suture knot placement can be an important yet difficult step. Additionally, after the knots are tied in the sutures, surgeons will generally cut that excess tails of the suture off so that only the necessary amount of suture remains at the repair site. However, such placement of knots and cutting of the knots typically requires the use of two separate tools, further complicating the surgical process.

Even when a device may incorporate the function of both cutting and pushing of the suture/knot, it would be helpful for a device to be operated with a single hand or a single finger (e.g., a thumb) on a hand to both engage the suture and later, cut the suture. Finally, it would be beneficial for a knot pusher/suture cutter device to include a safety (e.g., safety lock) to prevent the inadvertent activation of the cutter, which could prematurely cut a suture.

Described herein are apparatuses for pushing a knot of suture and cutting the suture that may address the problems and needs identified above.

SUMMARY OF THE DISCLOSURE

In general, described herein are surgical knot pusher and suture cutter apparatuses, and methods of using them to position a knot and cut the suture. These apparatuses (which include devices for knot pushing/suture cutting, and system including such devices) typically include a control that is configured to open a portion of the distal end of the apparatus for loading a suture laterally at the distal tip region; the same (or a different) control may be configured to drive a cutter for cutting a prescribed length of suture relative to a pushed knot. Any of the devices described herein may include a safety (e.g., safety release, cutter release, cutter safety, etc.) that may be normally engaged to prevent the cutter from cutting a suture in the distal end of the device, but may be selectively disengaged to allow the cutter to cut a suture. The safety may be positioned with the control on the handle of the device, so that a user may operate the control for opening/loading the device and for cutting the suture with a single finger (e.g., the thumb), and may engage/disengage the safety with another finger or fingers (e.g., the index finger). The safety may be disengaged, allowing cutting by the cutter, by pressing on the safety and concurrently activating the control to drive the cutter to cut the suture. Any of these devices may also include a lock, stop or other feature (such as a "lock out tab") that prevents the suture from falling out of the distal end of the device, even when force is applied against the loading portion of the device (e.g., an inner mandrel or inner member that can be displaced to allow loading of the suture) by a knot or other structure. Any of these device, and particularly those with a lock or other feature that prevents dropping of the suture even when applying force against the suture loading region, may also include a thumb ring at the proximal end that may be used by a surgeon to manipulate and position the device.

For example, any of the are surgical knot pusher and suture cutter apparatuses described herein may include: a handle; an elongate holding tube attached to the handle, the elongate holding tube including a lateral slot opening from a distal end of the holding tube and configured to allow a suture to pass therethrough; an inner member (also referred to herein as an inner mandrel) within the holding tube, wherein the inner member is axially movable relative to the holding tube and configured, when distally positioned, to capture the suture between the inner member and the holding tube; a tubular cutter around the holding tube, the cutter configured to be axially movable relative to the holding tube to cut an end of the suture when extended distally; a control on the handle configured to control the axial motion of both the inner member and the axial motion of the cutter; and a cutter release configured to prevent axial motion of the cutter unless the cutter release is disengaged.

The elongate holding tube is generally a cannula that includes an opening (cut-out region, slot, etc.) located laterally in the surface of the cannula body that is continuous with the distal tip of the device to allow access of at least a portion of the suture into the cannula body. Any of the apparatus may therefore include an elongate holding tube having an open lateral slot forming a generally J-shaped opening through the distal end of the holding tube and configured to allow a suture to pass therethrough. In some variations the lateral slot or opening is L-shaped, rather than J-shaped, or some other shape having an axial (distal-to-proximal) extending notch region and a radial extension (e.g., the base of the "L" or "J"); this region may also be connected to a shorter proximal-to-distal region that does not extend fully to the distal tip. The slot may be of any appropriate width and length. In general, the slot is wide enough to accommodate even a large-diameter suture. Further the slot extends completely through the elongate holding tube. The walls of the slot may be rounded or smoothed to prevent inadvertently cutting the suture. The wall of the slot may be selectively smoothed in some regions but not others (e.g., allowing cutting in some regions. The axial length of the region of the slot open to the distal end of the elongate holding tube may determine the length of the suture remaining after it has been cut (e.g., the distance from the knot to the cut end of the suture). This distance may be generally minimal (e.g., less than 5 mm), but of sufficient length to prevent the knot from coming off of the suture or untying. For example, in some variations the distance (e.g., the "height" of the J or L forming the J-shaped or L-shaped slot) is between about 5 mm and 0.2 mm, between about 5 mm and about .5 mm, between about 3 mm and about 1 mm, about 1.5 mm, about 2 mm, about 2.5 mm, etc.

Any of the apparatuses described herein may include an inner member that comprises a recessed region at the distal end extending longitudinally to form an opening between the inner member and an inner wall of the elongate holding tube. This inner member is configured to be biased so that it is held in the "at rest" state distally. In general, the inner member may match the inner diameter of the elongate holding tube, however at least the distal region may include a region that has a smaller outer diameter, and is therefore spaced apart (forming a cavity, notch, opening, spacing, etc.) relative to the elongate holding tube when the apparatus is at rest; when a suture is loaded into the elongate holding tube and the inner member is at rest, extended distally, the suture may be retained within the tip of the apparatus in the cavity/channel/opening formed by the inner wall of the elongate holding tube and the notched region of the inner member, and specifically the portion of the inner member that has the smallest outer diameter (OD), such as a notched region.

In some variations, as shown in FIGS. 1A-2D, the inner member may be held rotational fixed relative to the elongate holding tube. For example, the inner member may be positioned so that the region forming the notch with elongate holding tube is radially offset from the long (distal-to-proximal) portion of the lateral opening through the elongate holding tube, but aligned with the short leg of the opening, e.g., the a radial extension (e.g., the base of the "L" or "J" in the slot) and/or the this region may also be connected to a shorter proximal-to-distal region of the slot. The proximal portion of the suture may stick out of the knot pusher/suture cutter, while the distal portion of the suture exist the distal-facing opening in the apparatus. In use, a user may hold or pull the proximal end of the suture taught so that the suture can be put into the longitudinal (e.g., "J-shaped slot) opening in the elongate holding tube using an apparatus held entirely in the user's other hand, and once coupled to the suture, the device may be advanced distally (or pulled proximally) to push a suture; the same hand may be used to disengage the safety and cut the suture held in the distal end of the device by operating the single control of the device.

In any of the variations of the apparatuses described, the control may be a slider that is configured to be operated with a single finger to control the motion of both the inner member (e.g., sliding and/or rotation) and to control the axial motion of the cutter. For example, sliding the control (slider) proximally (back toward the user's hand) against a return or biasing force may "open" the lateral slot so that a suture can be captured therein. Releasing the slider, or moving the slider back distally, may restore the inner member (inner plunger member, etc.), closing off a portion of the lateral slot and may lock a suture within the cavity formed by the inner member and the inner diameter of a portion of the elongated holding tube.

The control comprises may be a button, knob, dial or slider. In general the slider may be configured to be operated with a single finger and to control the axial motion of the inner member when the slider is operated in a first direction and to control the axial motion of the cutter when the slide is operated in a second direction.

As mentioned, the inner member may be biased against sliding proximally and the cutter may be biased against sliding distally. In any of the apparatuses described herein the neutral position for the device may be configured with the lateral opening at least partially closed off by the inner member extended distally, while the cutter is retracted proximally.

Any of the apparatus variations described herein may include a safety, such as a cutter release. The safety may be referred to as a safety, cutter safety release, cutter release, or the like. The cutter release may generally include a button, slider, knob, latch, or any other manual control that can be activated by a user's hand. The cutter release may be, for example, a button. The cutter release may be located on the handle. For example, the cutter release may be located on an opposite surface from the control. In general the cutter release may be configured so that it engages the cutter ("tubular cutter") and/or the control (e.g., slider) on the handle to prevent the cutter from being advanced distally to cut a suture held in the distal end of the device. In some variations the cutter release may reside in a track or path of the slier and/or cutter, blocking the control and/or cutter from advancing distally until the cutter release is disengaged by manually activating, e.g., pushing, sliding, switching, etc., the cutter release. For example, the cutter release may be biased to engage with the control to prevent the cutter from advancing distally until the cutter release is engaged.

Any appropriate cutter may be used, including tubular cutter that is poisoned over or at least partially over the elongate holding tube (and/or inner member). The cutter may include a distal-facing cutting face for cutting through the region of the suture extending out of the opening from apparatus, such as the region of the later slot through the elongate holding tube that overlaps with the smaller diameter region of the inner member. For example, the tubular cutter may include a distal-facing tapered edge that is configured to cut suture. A tapered edge that tapers down into an annular cutting ring may be preferable because it allows the suture to be cut from any angle or orientation of the suture relative to the elongate body of the apparatus (e.g., the distal end of the device).

For example, any of the surgical knot pusher and suture cutter apparatuses may include: a handle; an elongate holding tube attached to the handle, the elongate holding tube including an open lateral slot forming a generally J-shaped opening through the distal end of the holding tube and configured to allow a suture to pass therethrough; an inner member within the holding tube and axially movable relative to the holding tube, the inner member configured, when distally positioned, to capture the suture between the inner member and the holding tube; a tubular cutter extending around the holding tube, the cutter configured to be axially movable relative to the holding tube to cut an end of the suture; a slider on the handle and configured to be operated with a single finger and to control the axial motion of the inner member when the slider is operated in a first direction and to control the axial motion of the cutter when the slide is operated in a second direction; and a cutter release configured to prevent axial motion of the cutter unless the cutter release is engaged; wherein the inner member is biased against sliding proximally and the cutter is biased against sliding distally.

Any of the surgical knot pusher and suture cutter apparatuses may include: a handle; an elongate holding tube attached to the handle, the elongate holding tube including an open lateral slot forming a generally J-shaped opening through the distal end of the holding tube and configured to allow a suture to pass therethrough; an inner member within the holding tube and axially movable relative to the holding tube, the inner member configured, when distally positioned, to capture the suture between the inner member and the holding tube, wherein the inner member comprises a recessed region at the distal end extending longitudinally to form an opening between the inner member and an inner wall of the elongate holding tube; a tubular cutter extending around the holding tube, the cutter configured to be axially movable relative to the holding tube to cut an end of the suture, wherein the tubular cutter comprises a distal-facing tapered edge; a slider on the handle and configured to be operated with a single finger and to control the axial motion of the inner member when the slider is operated in a first direction and to control the axial motion of the cutter when the slide is operated in a second direction; and a cutter release button located on the handle opposite the slider and configured to prevent axial motion of the cutter unless the cutter release is engaged, wherein the inner member is biased against sliding proximally and the cutter is biased against sliding distally.

Also described herein are methods of using an apparatus for knot pushing and suture cutting as described herein. In general, these methods including coupling the suture to the distal end of the apparatus, pushing the knot distally, and disengage the cutter release (safety), and cutting the suture. In some variations, all of these steps may be performed with a single hand, using only two fingers (or two finger controls); a first, e.g., thumb, control for both loading the suture into the distal end of the device by opening and closing a lateral slot, and for activating the cutter to cut a suture loaded in the distal end; and a second, e.g., index finger, control for disengaging the cutter safety (cutter release).

For example, a method of pushing a suture knot with a surgical knot pusher and suture cutter apparatus may include: sliding a control on a handle of the apparatus proximally to retract an inner member proximally; placing a suture into a lateral side opening of an elongate holding tube of the apparatus so that the suture extends from the distal end of the apparatus and also from the lateral side opening; advancing the inner member distally within the elongate holding tube to secure the suture between the inner member and the elongate holding tube; pushing a knot on the suture by advancing the apparatus distally over the suture; engaging a cutter release on the handle to permit a tubular cutter on the outside of the elongate holding tube to be advanced distally; sliding the control on the handle of the apparatus distally to advance the tubular cutter after engaging the cutter release; and cutting the suture using a distal-facing beveled edge of the tubular cutter. Some of these steps may be omitted, and additional steps added.

In any of the methods described, the step of sliding the control on the handle of the apparatus proximally to retract the inner member proximally may comprise sliding the control proximally with a single finger, wherein the control comprises a slider. Sliding the control on the handle of the apparatus proximally to retract the inner member proximally may comprise sliding the control proximally against a bias force operating to keep the inner member positioned distally.

The step of placing may include hooking the suture into a generally J-shaped opening or L-shaped (lateral slot) through the distal end of the holding tube. Advancing the inner member distally may comprise releasing the control to permit the inner member to advance distally. Advancing the inner member distally may include sliding the control distally to advance the inner member distally. In general, engaging the cutter release may include pushing on the cutter release with an index finger of a hand while a thumb of the hand operates the control on the handle. Sliding the control on the handle of the apparatus distally may include sliding a slider with a thumb while concurrently pushing on the cutter release with a finger.

Any of the methods described herein may include loading a length of suture into the distal end of the device (e.g., the L-shaped or J-shaped lateral slot) so that the length of suture extends at one end distally from the device (e.g., where the knot to be pushed may be located), and at the other end laterally from the slot; the lateral exit allows the device to be cut by the sliding cutter. Any of these methods may include loading the length of suture into the device by first displacing the inner member (inner mandrel) to expose a continuous opening from the distal end and along the lateral slot and then loading the suture length into the opened lateral slot so that one end of the suture extends distally and a second end extends laterally. In some variations the inner member (mandrel) is displaced by axially sliding the inner member/mandrel proximally or distally. In some variations the inner member (mandrel) is displaced by rotating the inner member/mandrel so that a notch on the side of the inner mender/mandrel is aligned with the lateral slot at the distal end of the device. In any of these variations the method may also include locking or securing the inner member (mandrel) in position after loading so that it cannot be accidentally moved (slide axially and/or rotated) and allow the suture to escape from the distal end of the device. For example, the apparatus may include a lock (e.g., lock out tab as described below) that engages the inner mandrel and prevents it from sliding axially when engaged; the lock (lock out tab) may be released/overridden by the user (e.g., surgeon) manipulating a control, such as a lock release or the control for actuating the inner member/mandrel, allowing the inner member/mandrel to be moved axially and/or rotated. Further, any of these methods may include one or more steps of engaging the device through a proximal thumb ring. For example, a physician may engage with the device by placing her/his thumb into the thumb ring and manipulating the device to push a knot along the suture. Other fingers, as mentioned above, may be used to manipulating the loading/unloading (e.g., the inner member) and cutting.

In some examples, described herein are surgical knot pusher and suture cutter apparatuses including: a handle; an elongate holding tube attached to the handle, the elongate holding tube including a lateral slot opening from a distal end of the holding tube and configured to allow a suture to pass therethrough; an inner mandrel within the holding tube, the inner mandrel having a notch extending proximally from a distal end of the inner mandrel along a side region of the inner mandrel, wherein the inner mandrel is axially movable relative to the holding tube and is configured to capture the suture between the inner mandrel and the holding tube when the inner mandrel is extended distally; a tubular cutter around the holding tube, the cutter configured to be axially movable relative to the holding tube to cut an end of the suture when the tubular cutter is extended distally; a control on the handle configured to control the axial motion of both the inner mandrel and the axial motion of the cutter; a lock out tab coupled to the inner mandrel and configured to prevent the axial movement of the inner mandrel until the lock out tab is released; and a cutter release configured to prevent axial motion of the cutter unless the cutter release is disengaged.

Any of these apparatuses may also include a thumb ring at the proximal end of the device, as described above. The elongate holding tube may include an open lateral slot forming a generally L-shaped or J-shaped opening through the distal end of the holding tube that is configured to allow a suture to pass therethrough.

The notch of the inner mandrel (inner member) may include a recessed region at the distal end extending longitudinally to form an opening between the inner mandrel and an inner wall of the elongate holding tube. A mandrel may be any elongate member (e.g., rod, tube, shaft, column, etc.) that may be displaced to allow loading of the suture length. The distal end of the mandrel (or in some variations, the distal end of the holding tube) is typically configured to provide a surface against which a knot may be pushed.

As mentioned above, and shown in more detail below, the control for moving the cutter and/or the inner member/mandrel may be a slider that is configured to be operated with a single finger. For example, the slider may control the axial motion of both the inner mandrel and to control the axial motion of the cutter. In some variations, the control may comprise a slider configured to be operated with a single finger and to control the axial motion of the inner mandrel when the slider is operated in a first direction and to control the axial motion of the cutter when the slider is operated in a second direction.

In general the cutter may be biased (e.g., by include a bias or spring element) that provides a force to urge the cutter proximally; to operate the cutter, the user may push against the bias to cut a suture extending laterally from the apparatus. Similarly, in some variations the inner member/mandrel may be biased (e.g., by including a bias or spring element) that urges and holds the inner member distally; when loading the device with a suture, the inner member may be slid proximally by applying force against this bias. For example, an apparatus may include a first bias applying force opposing a proximal movement of the inner mandrel within the holding tube and a second bias applying force to oppose a distal movement of the tubular cutter relative to the holding tube. In addition to (or in some variations, instead of) the bias, one or more locks may be included to prevent the cutter and/or the inner member/mandrel from moving until the lock is released.

For example, any of these variations may include a cutter release that disengages a locking element holding the cutter in place proximally relative to the distal end of the elongate holding tube. The cutter release may be a button. The cutter release may cause the lock (which may be a latch, clasp, clamp, or the like, e.g., holding the cutter proximally) to disengage when activated, allowing the cutter to be moved distally. In some variations the cutter release is located on the handle on an opposite surface from the control. The cutter release may be biased to engage with the control to prevent the cutter from advancing distally until the cutter release is disengaged.

In variations in which the inner member/mandrel is axially movable (slideable) to open the lateral slit on the distal end of the elongate holding tube, a lock out tab may be configured to be released by the operation of the control. In some variations the lock out tab is a strip of material (e.g., rigid material) that connects to the inner member and another portion of the device (e.g., the handle) to hold it secure relative to the elongate holding tube. This may prevent the inner member from sliding proximally when the knot is pushed or pulled against the distal end of the inner member/mandrel, which could otherwise disengage the inner member and allow the suture to fall out of the apparatus. For example, a lock out tab may be configured to be released by deflecting the lock out tab away from the inner mandrel with the application of a threshold force.

In some examples a surgical knot pusher and suture cutter apparatus includes: a handle; an elongate holding tube attached to the handle, the elongate holding tube including an open lateral slot forming a generally L-shaped or J-shaped opening through the distal end of the holding tube and configured to allow a suture to pass therethrough; an inner mandrel within the holding tube wherein the inner mandrel is axially movable relative to the holding tube, the inner mandrel configured to capture the suture between the inner mandrel and the holding tube when the inner mandrel is distally positioned; a tubular cutter extending around the holding tube, the cutter configured to be axially movable relative to the holding tube to cut an end of the suture; a slider on the handle and configured to be operated with a single finger and to control the axial motion of the inner mandrel when the slider is operated in a first direction and to control the axial motion of the cutter when the slide is operated in a second direction; a lock out tab coupled to the inner mandrel and configured to prevent the axial movement of the inner mandrel until the lock out tab is released; and a cutter release configured to prevent axial motion of the cutter unless the cutter release is disengaged; wherein the inner mandrel is biased against sliding proximally and the cutter is biased against sliding distally.

Also described herein are apparatuses in which the inner member (e.g., mandrel) is a rotatable member that includes a notch or other cut-out region extending at least along a side portion of the distal end of the inner member. By rotating this inner member, the lateral slot in the elongate housing may be aligned with the notch in the inner member so that a suture can be loaded into the lateral slot and extend distally from the distal end of the apparatus and laterally from the proximal end of the apparatus.

For example, described herein are surgical knot pusher and suture cutter apparatuses that include: a handle; an elongate holding tube attached to the handle, the elongate holding tube including a lateral slot opening from a distal end of the holding tube and configured to allow a suture to pass therethrough; an inner mandrel within the holding tube, the inner mandrel having a notch extending proximally from a distal end of the inner mandrel along a side region of the inner mandrel, wherein the inner mandrel is rotatably movable relative to the holding tube and is configured to capture the suture between the inner mandrel and the holding tube when the notch is rotated away from the lateral slot opening; a tubular cutter around the holding tube, the tubular cutter configured to be axially movable relative to the holding tube to cut an end of the suture when extended distally; a first control on the handle configured to control the axial motion of the cutter; and an inner mandrel control on the handle configured to rotate the inner mandrel relative to the holding tube. These apparatuses may also include a stop configured to prevent axial movement of the inner mandrel within the holding tube. For example, the proximal end of the apparatus may include a collar or other region that engages a lip preventing it from being moved axially (distally and proximally) within the elongate holding tube; the lip and collar region form one variation of a stop.

As mentioned above, any of these variations may include a thumb ring at the proximal end of the device that may be used by a surgeon or other medical provider (user) using the device to manipulate/hold the device. The control may comprise a slider configured to be operated with a single finger to control the axial motion of the cutter. Any of these apparatuses may also include a bias applying force to oppose a distal movement of the tubular cutter relative to the holding tube.

Any of these apparatuses may also include a cutter release configured to prevent axial motion of the cutter unless the cutter release is disengaged.

In some variations of the apparatus, the inner mandrel is rotationally biased so that the notch is rotated away from the lateral slot opening. For example, the control for loading (by rotating the inner member/mandrel) may be operated against the biased position in which the distal end is 'closed'. The bias may be a mechanical bias element, and may automatically return the inner member to a preset position with the notch being rotated away from the lateral slot. In some variations the inner member may be biased so that the notch is aligned with the lateral slot (in an 'open' configuration).

For example, a surgical knot pusher and suture cutter apparatus may include: a handle; an elongate holding tube attached to the handle, the elongate holding tube including a lateral slot opening from a distal end of the holding tube and configured to allow a suture to pass therethrough; an inner mandrel within the holding tube, the inner mandrel having a notch region extending proximally from a distal end of the inner mandrel along a side region of the inner mandrel, wherein the inner mandrel is rotatably movable relative to the holding tube but is axially fixed relative to the holding tube, wherein the inner mandrel is configured to capture the suture between the inner mandrel and the holding tube when the notch is rotated away from the lateral slot opening; a tubular cutter around the holding tube, the tubular cutter configured to be axially movable relative to the holding tube to cut an end of the suture when extended distally; a first control on the handle configured to control the axial motion of the cutter; an inner mandrel control on the handle configured to rotate the inner mandrel relative to the holding tube; and a thumb ring at the proximal end of the device.

BRIEF DESCRIPTION OF THE DRAWINGS

FIG. 3A shows a close-up of the distal end of the apparatus of FIGS. 1A-1C where the inner member has been retracted proximally.

FIG. 3B shows movement of the actuator on the handle to retract the inner member.

FIG. 4 shows loading of a suture into the apparatus of FIGS. 1A-1C.

FIGS. 5A and 5B show placement of the apparatus of FIGS. 1A-1C against a suture knot.

In FIG. 8A, the inner member (mandrel) is in the rest configuration, biased with the inner member distally extended. In FIG. 8B, the inner member is retracted proximally against the biasing force, so that the distal end is in a loading position. In FIG. 8C, a suture is loaded into the distal end in which the inner member is proximally retracted. In FIG. 8D the inner member is released and extended distally, securing the suture within the distal tip of the apparatus. In FIG. 8E the cutter is extended distally so that the sharp (beveled) distal end cuts the suture held in the lateral (L-shaped or J-shaped) slot.

In FIG. 11A, the apparatus is shown in a neutral position with the inner member having a notch (a skived distal end region in this example) that is rotated away from the lateral slot formed in the elongate holding tube. The apparatus maybe locked in this position. FIG. 11B illustrates the rotation of the inner member/mandrel, e.g., by activation of a rotation control, so that the notch region is open towards the lateral slot in the elongate holding tube, as shown in FIG. 11C. FIG. 11D illustrates loading a length of suture, proximal to a knot, into the lateral slot once the inner member/mandrel is rotated to align with the lateral slot. FIGS. 11E and 11F illustrate the return of the inner member/mandrel to the closed and locked position.

FIG. 12A shows an inner mandrel having a notch region formed in one lateral side of the member (shown as a skived region); this inner member is shown in the device of FIGS. 7A-8E. In FIG. 12B the distal end of the inner member is similar to the rotatable inner member shown in FIGS. 10A-11F. FIG. 12B shows an inner member similar to the variation shown in FIG. 12, but with the cut-out region (notch) extending along the majority of the length of the inner member, rather than just the distal end region.

In FIG. 13A, the inner member is shown into a closed configuration so that the notch in the side of the inner member is not aligned with the lateral slot in the elongate holding tube. In FIG. 13A, the inner member (which in this example is a tube having a lateral cut-out region or slot) is rotated to align with the slot in the elongate holding tube. FIG. 13C illustrates loading of a length of suture into the distal end of the apparatus. FIG. 13D illustrates locking of the length of suture into the distal end of the device by rotating the inner member back (or allowing the inner membrane to rotate back) to the closed position.

DETAILED DESCRIPTION

Figure 1A:
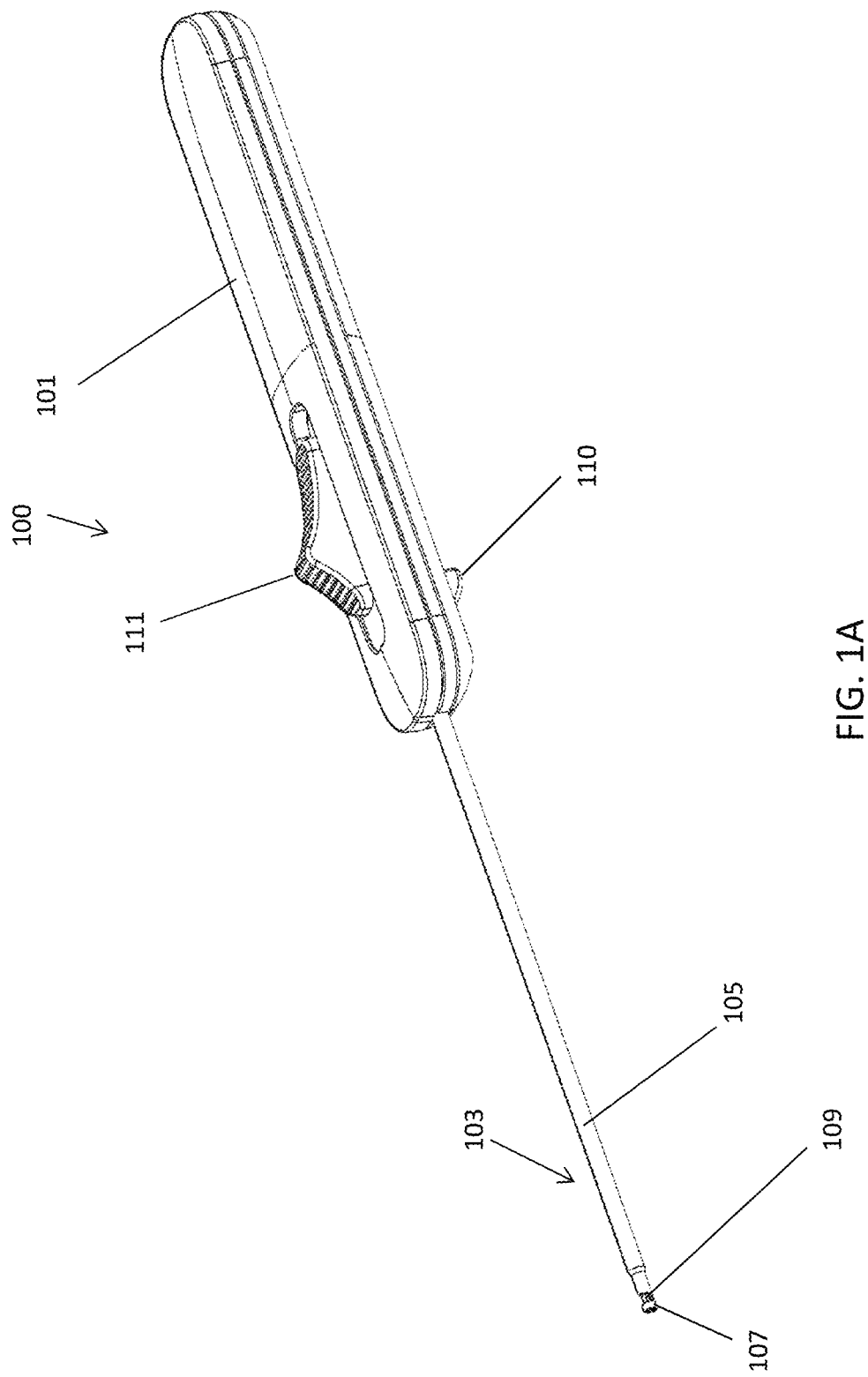
FIGS. 1A-1C show a knot pusher and suture cutter apparatus in front perspective, bottom perspective and side views, respectively.

Described herein are combination knot pusher and suture cutter apparatuses for manipulating (e.g., pushing) a pre-tied knot in a suture to a desired location and then for cutting excess suture proximal to the knot. The apparatuses described herein may include a handle attached to an outer holding tube (or pushing member). The handle may include a thumb ring at the proximal end for holding the device. The outer holding tube typically extends around an inner rod (also referred to as an inner member or inner mandrel). The distal ends of the outer holding tube and inner member may generally be configured to engage a suture in a laterally (proximally-to-distally) extending region of the inner member and the outer holding tube, so that the distal end of the device may be used to push a pre-tied knot, which typically has a diameter greater than the diameter of a distal-facing opening between the holding tube and the inner member, along the suture strand by advancing the apparatus distally. A cutter (cutting member) can extend around the outer tube and can be moved axially to cut the proximal end of the suture that extends from a lateral opening in the apparatus. The cutter may be referred to as a tubular cutter. A control or actuator on the handle (e.g., slider, knob, etc.) can be operated to move the inner member (e.g., inner mandrel) relative to the outer holding tube, exposing a lateral slot in the outer holding tube and a notch in the inner member, and allowing access to a region between the inner member and the outer holding tube for loading of the suture though the lateral slot. Once loaded, the outer slot can be closed off by moving the inner member. For example, the inner member may be moved by sliding it axially (e.g., withdrawing it proximally) relative to the outer holding tube and/or by rotating it within the outer holding tube.

A second control (e.g., a trigger, slider, etc.) that is connected to the actuator can provide a safety release (cutter release) to prevent undesired distal movement of the actuator and/or cutter, and thus prevent undesired cutting of the suture.

In any of these variations, the inner member may be locked in position when not being actuated, to prevent the suture from disengaging with the distal end of the apparatus. For example, in rotational variations, the inner member may be configured to rotate in the elongate axis, but not to slide proximally, and may include a lock to prevent axial sliding. In some variations the rotational motion may also be prevented by a lock (e.g., pin, clamp, etc.) that holds the inner member in a fixed rotation relative to the outer holding tube. The inner member (inner mandrel) lock may be released by the same control that allows the user to rotate the inner member to load the device. Similarly, apparatuses in which the inner member is configured to slide axially and allow access of the suture for loading into the outer holding tube through the lateral slot may include a lock that prevents the inner member from sliding except when the lock is released. For example, the control for actuating the inner member movement may disengage the lock, which may also be referred to as an inner member lock or lock-out member, and may be configured as a pin, a lock out tab, a clamp, etc.

Any of the apparatuses described herein may be dimensioned for use with surgical sutures placed in a knee, and may further be dimensioned for arthroscopic use. For example, the outer diameter of the inner member (excepting the lateral notch region, e.g., in some variations a narrower region forming the laterally extending space, for holding the suture in conjunction with the inner wall of the outer holding tube), may be between about 0.5 and 4 mm (e.g., about 2 mm). The inner diameter of the cutter may be between about 1 mm and about 5 mm (e.g., 2.75 mm). The elongated length of the holding tube may be between about 6 and about 20 cm, e.g., between about 10 cm and about 11 cm.

Figure 1B:
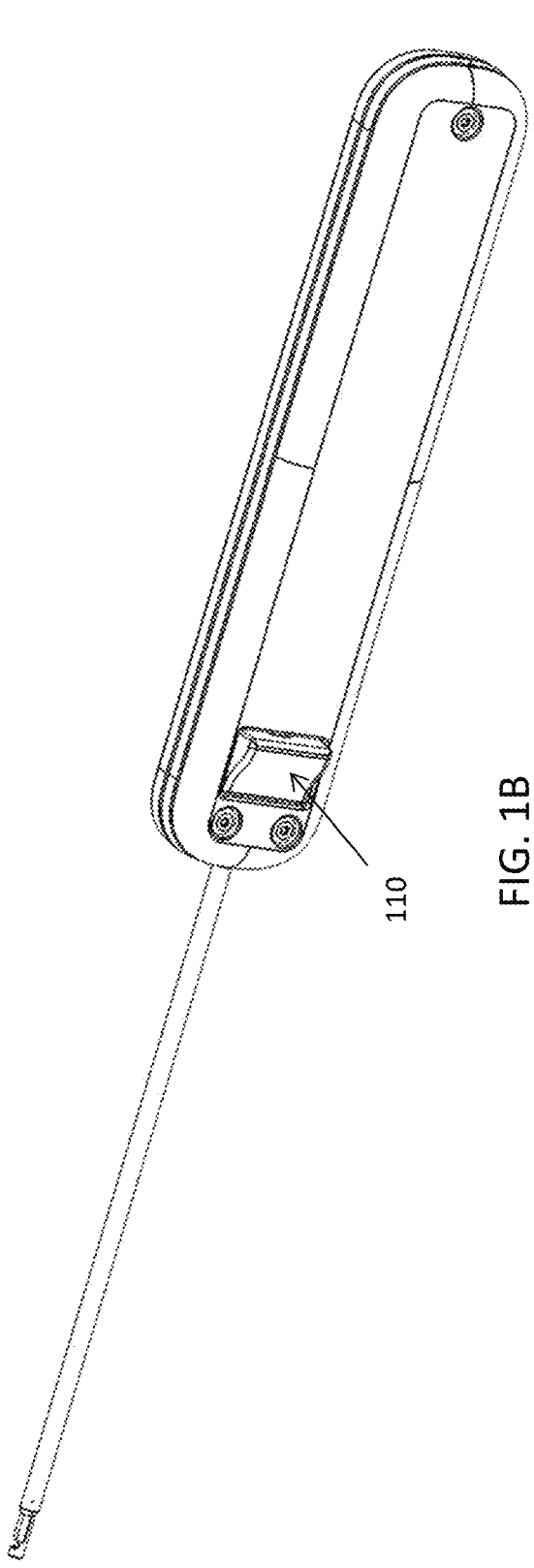
Figure 1C:
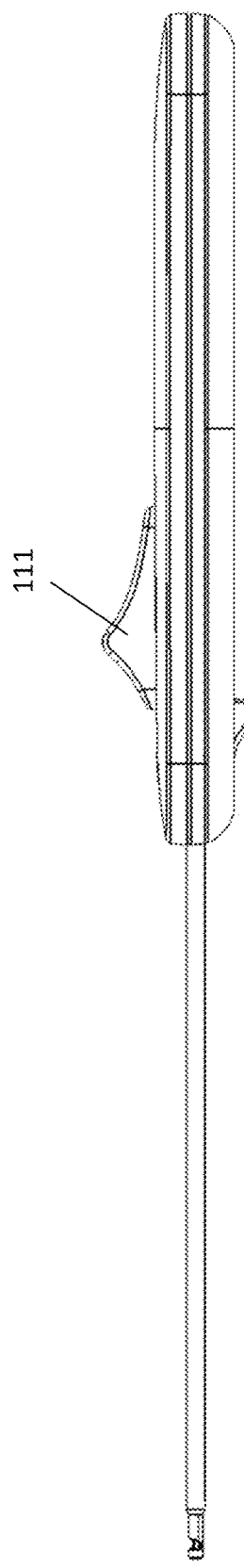

FIGS. 1A-1C illustrate one variation of an apparatus as described herein. In this example, the suture is loaded into the distal end, so that a knot on the suture is distal to the distal end, and a proximal region of the suture extends laterally from the lateral slot in the outer holding tube. In this example, the inner member is an inner mandrel that is axially slideable and includes a notch region on a lateral side of the inner member; when loaded, a length of the suture may be held in this cannel between the inner member and the outer holding tube.

For example, with reference to FIGS. 1A-2D, a surgical knot pushing and suture cutting apparatus 100 includes a handle 101 and an elongate surgical mechanism 103 extending therefrom. The surgical mechanism 103 includes an inner member 109 within a pushing member (elongate holding member) 107, which is disposed within a cutting member 105. The elongate holding (pushing) member 107 can be fixedly attached to the handle 101 while the inner member 109 and cutting member 105 may be independently axially movable relative to the holding/pushing member 107 and the handle 101. In any of these variations described herein, the cutting member 105 and the elongate holding member 107 can be hollow while the inner member 109 is solid; in some variations (shown below), the inner member may be hollow or partially hollow (e.g., near the distal end). Further, the cutting member 105, 105' can extend coaxially at least partially around the holding member (pushing member) 107, which extends coaxially around the inner member 109.

Figure 2A:
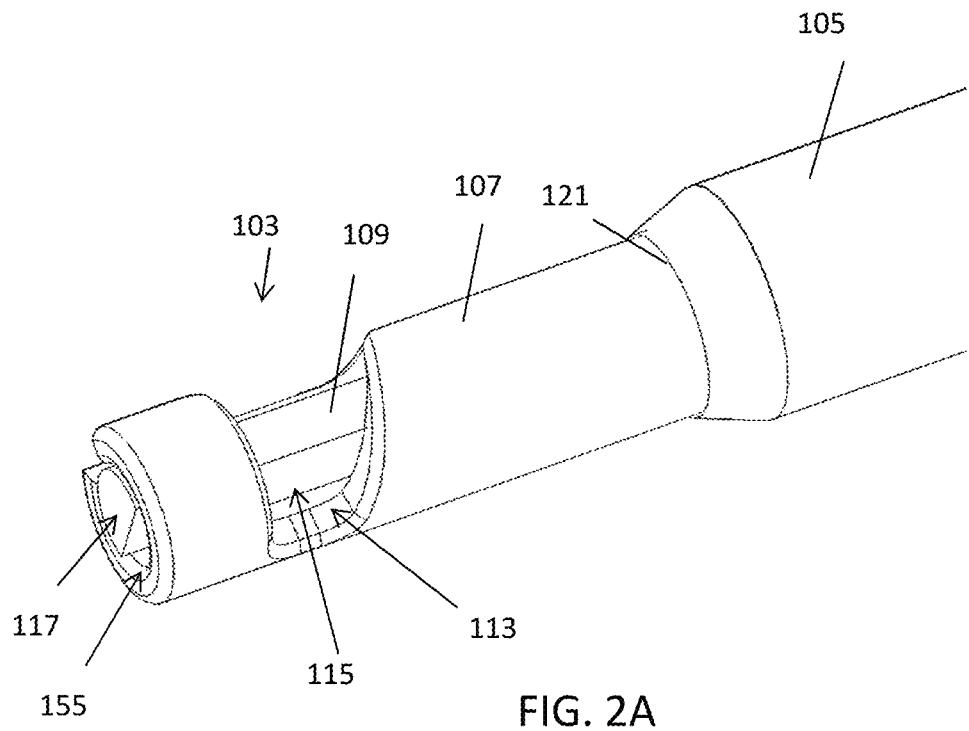
FIGS. 2A and 2B show close-ups of the distal end of the apparatus of FIGS. 1A-C.
Figure 2B:
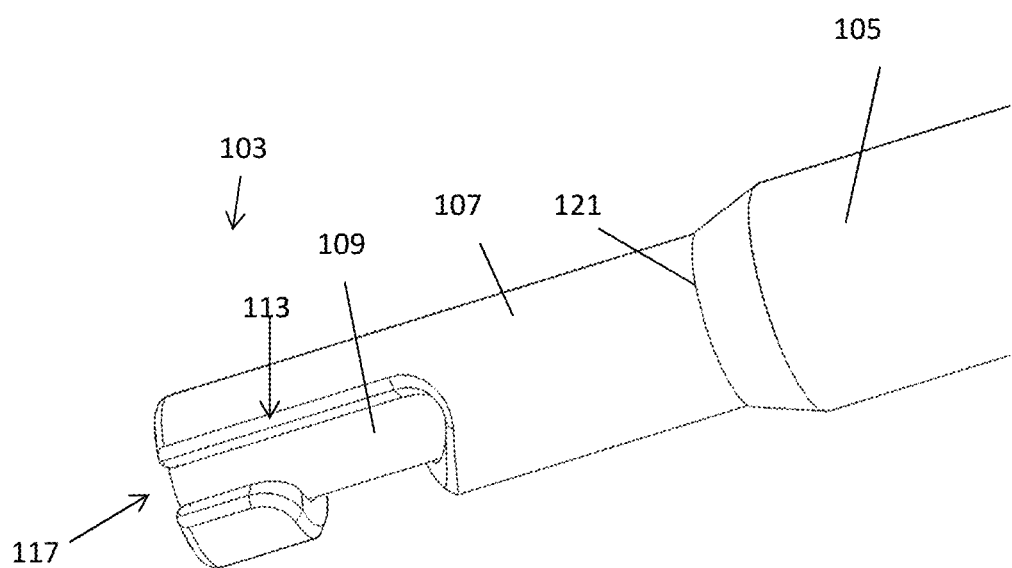

The holding member 107 may also be referred to as a pushing member (or pushing/holding or holding/pushing member) because it can both hold the suture and push the suture knot. The holding/pushing member 107 can include an elongate (laterally extending) cut-out portion 113 in the wall thereof configured to form, in conjunction with the inner diameter of the elongate holding tube wall, a longitudinally extending passage or channel 155 for a suture to pass through. For example, as shown in FIGS. 2A and 2B, the elongate cut-out portion can include a circumferentially extending portion around approximately half of the circumference of the pushing member 107 connected to an axially extending portion extending to the distal end 117 of the device 100. Further, the inner member 109 can include a notch 115 extending substantially along the length of the cut-out portion 113, 113' when the distal edges of the inner member 109 and pushing member 107 are aligned. The cut-out portion 113, 113' may be L-shaped, or J-shaped, as mentioned above. The leg portion of the notch (e.g., forming the base of the L or J may be any appropriate length, and may extend transverse to the lateral portion of the notch (e.g., at an angle of between about +45 and −45 degrees).

The cutting member 105, 105' can include a cutting edge around all or a portion of the distal edge of the cutter. For example, the distal edge 121 of the cutter 105 (as shown in FIGS. 2A-2B) may be tapered to point (forming a circumferential cutting edge) in cross-section. As noted above, the cutting member 105 can be positioned around the pushing member 109 and inner member 107.

Further, the handle 101 can include a control (e.g., slider, actuator, etc.) 111 configured to retract the inner member 109 and/or actuate the cutting member (cutter) 105. The handle 101 can also include a control (e.g., trigger, slider, button, etc.) 110 as part of the safety, or cutter release, that is configured to prevent distal movement of the actuator 111 and/or cutter 105 until the trigger is compressed. The safety (cutter release) may be attached to the actuator 111 and/or to the cutter 105. By using a single actuator 111 to both move the inner member for suture loading and to actuate the cutter to cut the suture, the handle 101 can advantageously be held still and/or kept in position throughout the surgery without requiring rotation or repositioning of the surgeon's hand relative to the handle. Similarly, the safety may be actuated by the same hand. The surgeon can thus actuate both mechanisms and hold the handle with a single handle. Further, the safety 110 can advantageously prevent the cutting mechanism from being activated until desired, thereby preventing accidental cutting of the suture during use.

Figure 2C:
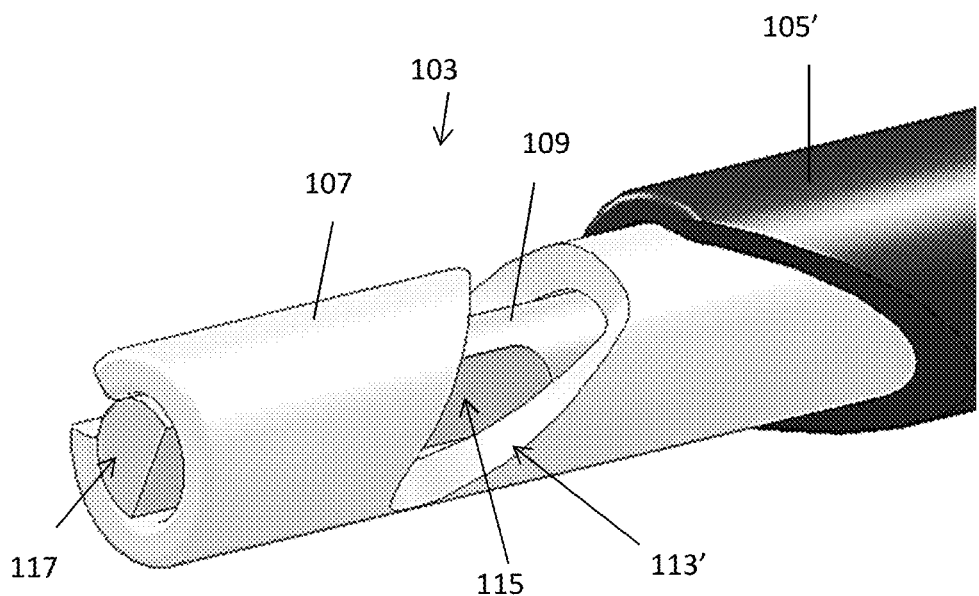
FIGS. 2C and 2D show alternative variations of the distal end (including the cutter tube) of an apparatus such as the one shown in FIGS. 1A-C.
Figure 2D:
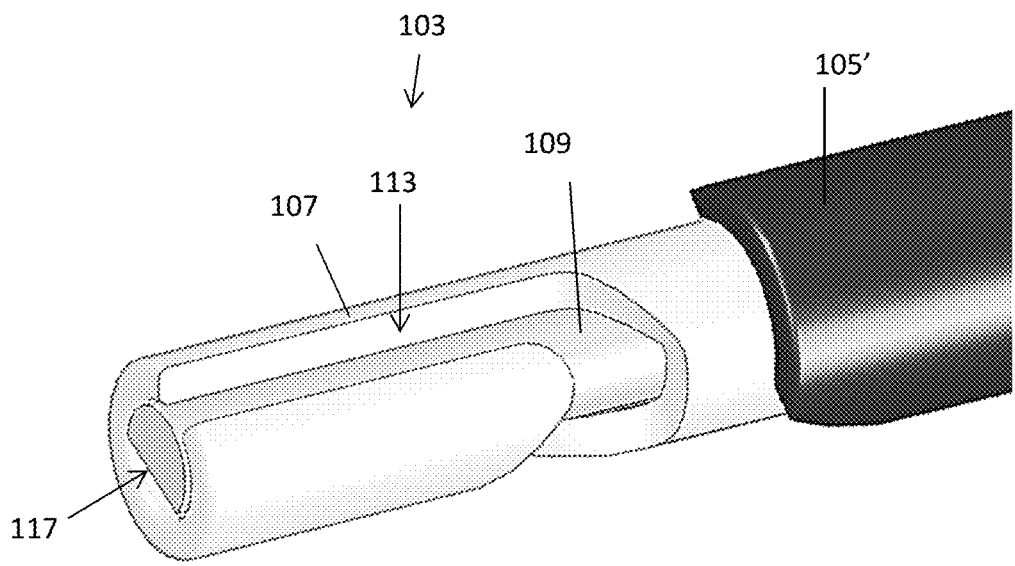

In the at-rest position of the device 100 shown in FIGS. 1A-1C, 2A-2B, the cutting member 105, 105' can be positioned proximally of the cut-out portion 113, 113' and notch 115 while the distal ends of the pushing member 107 and the inner member 117 can be substantially aligned. In some variations, to prevent accidental unloading of a suture when held within the loading region FIGS. 2A-2B and 2C-2D illustrate alternative variations of cutting member (tubular cutter) 105, 105'. In FIGS. 2A-2B, the cutting member extends around the holding/pushing tube 107 and the inner member 109, and has a tapered cutting edge 121 all the way around the distal end of the cutting member. In FIGS. 2C-2D, the cutting member is beveled over the region overlapping with the window of the cut-out region in which the tail of the suture will reside, but not over the portion of cut-out region 113' that extends laterally (in the distal to proximal direction). In FIGS. 2A-2B the cut-out region 113 is roughly L-shaped, and includes a lateral slot opening from the distal end 117 of the holding/pushing tube 107 and is configured to allow a suture to be loaded into the elongate distal-to-proximal portion that connects to the distal end 117. The section of the cut-out region 113 that is transverse to the distal-to-proximal axis of the apparatus (the "base" of the L- or J-shape) form a window from which the tail of a suture, once held in the apparatus, extends, as illustrated below. This window is formed by the notched portion (smaller diameter portion) of the inner member 109 and the cut-out portion of the holding/pushing member 107. In FIGS. 2C-2D the transverse portion of the cut-out region 113', forming a window from which the suture tail may extend, turns back in the distal direction of the apparatus.

Figure 5B:
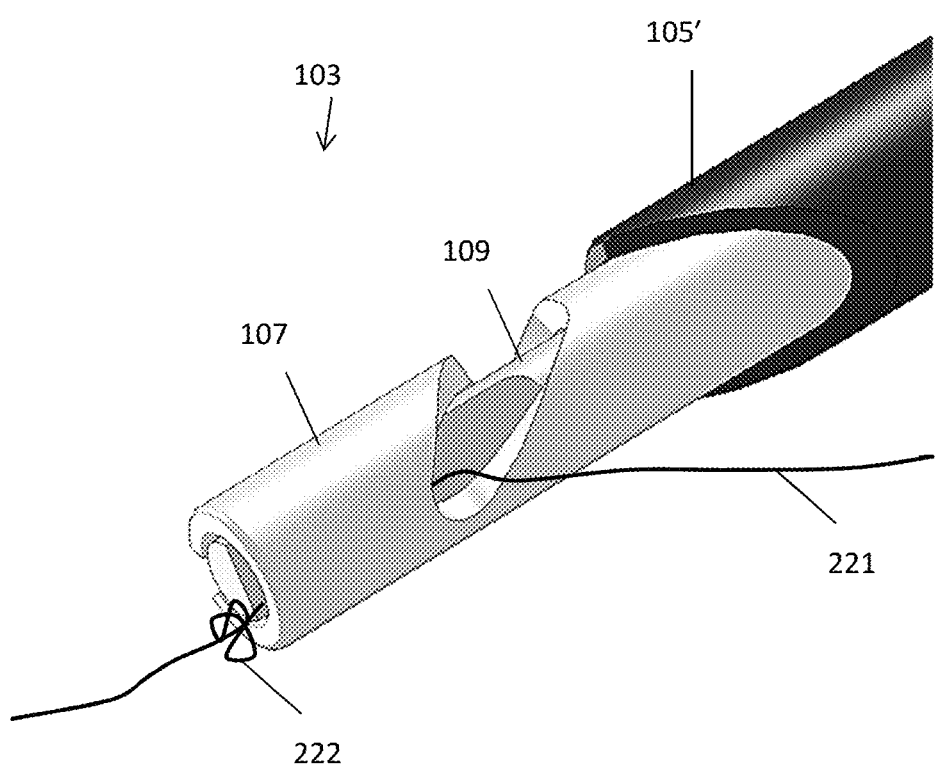

Referring to FIGS. 3A and 3B, to use the device 100, the control/actuator 111 can be pulled proximally by a surgeon to retract the inner member 109. By retracting the inner member, the lateral slot (cut-out portion) 113' can be exposed, thereby opening the lumen of the outer holding tube 119 within the pushing member (outer holding tube) 107. Referring to FIG. 4, a suture 221 having a pre-tied slideable knot 222 thereon can then be loaded or threaded mid-line into the access channel formed by moving the inner member away from the lateral slot 113' in the outer holding tube. As shown in FIGS. 5A and 5B, the inner member 109 can then be moved distally (i.e., via release of the actuator 111) to lock the suture within the access slot 119. While holding the proximal end of the suture (e.g., using a thumb ring, not shown in FIGS. 5A and 5B), the device 100 can then be slid distally over the suture 221 until the distal end of the device hits a pre-tied knot 222. After reaching the knot 222, the device 100 can be further pushed distally as the proximal end of the suture 221 is held, thereby pushing the knot 222 distally until the knot reaches the desired location, such as a repair site, and can be secured (e.g., cinched).

Figure 6A:
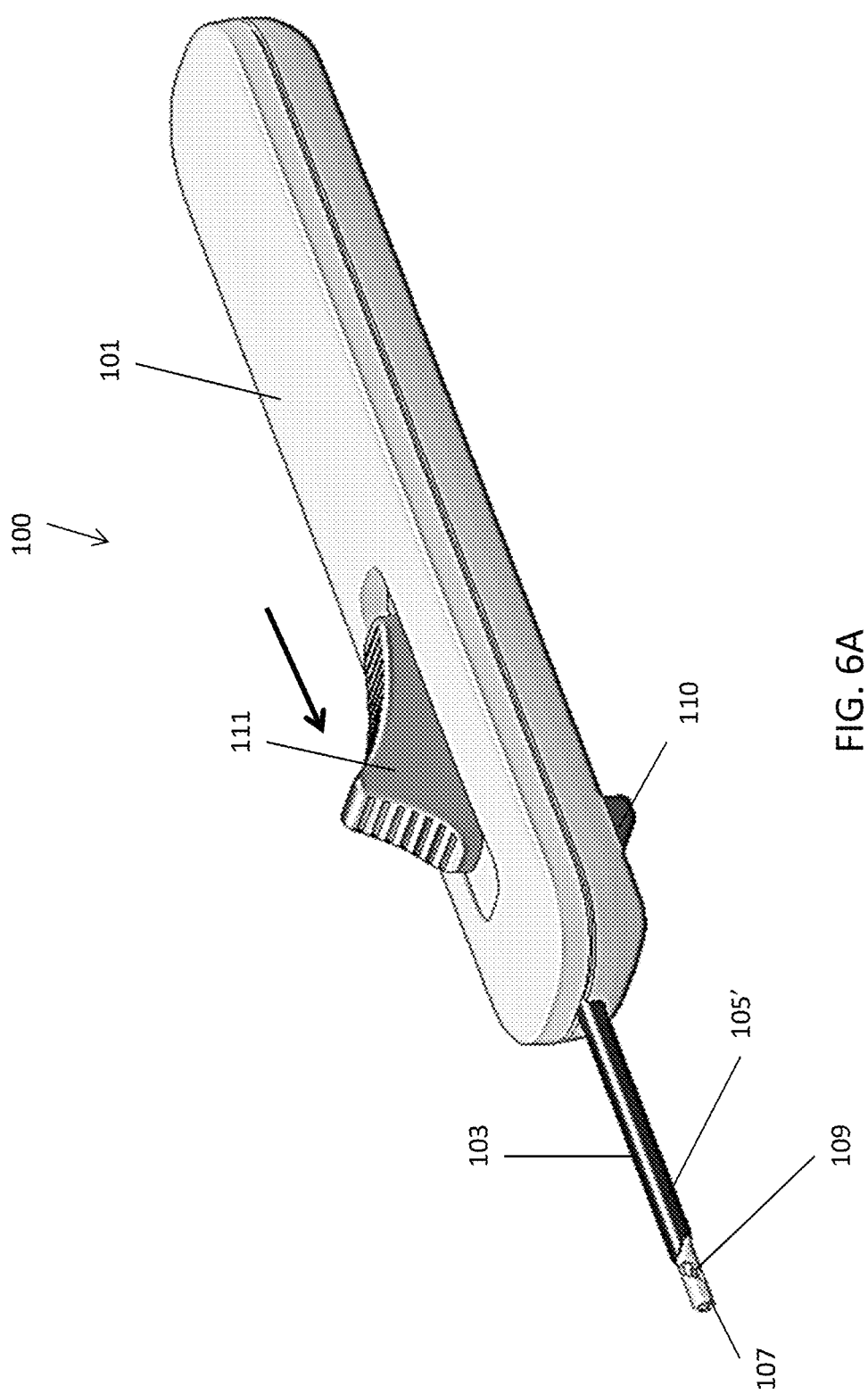
FIG. 6A shows movement of the actuator of the apparatus of FIGS. 1A-1C distally to activate the cutter.
Figure 6B:
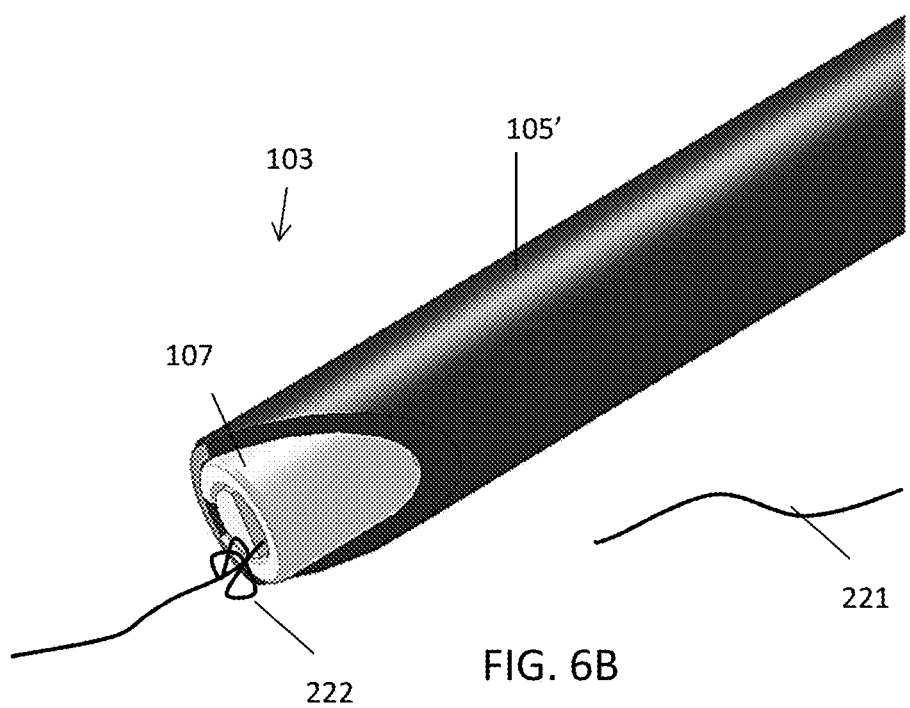
FIG. 6B shows a close-up of the distal end as the cutter is moved proximally to remove the tail of the suture.

As shown in FIGS. 5B and 6A-6B, when the knot 222 has been fully advanced to the repair site, the trigger 110 can be compressed by the surgeon to disengage the safety (and/or engage the safety release), thereby allowing the slider actuator 111 to be moved distally by the surgeon. This distal movement moves the cutting member 109 distally, which can cut off the end of the tail of the suture 221. After use, the remaining length of the tail of the suture 221 can be very small, e.g., between about 0.5 mm and about 3 mm, between about 1 mm and about 2 mm, about 1.5 mm, etc. The length of the tail may be determined by the location in the lateral slot wherein the suture exits, such as a crotch or cul-de-sac region of the J-shaped or L-shaped lateral slot. Thus, the distance from the exit region (at a distal most region that is offset from the long leg of the notch) may be chosen to determine the length of the tail (e.g., less than 4 mm, less than 3 mm, less than 2 mm, less than 1.5 mm, less than 1 mm, less than 0.5 mm, etc.).

Advantageously, the device described herein can provide a single arthroscopic instrument that allows a surgeon, after forming a pre-tied knot outside of the body, to both push the pre-tied knot through the arthroscopic portal down to the repair site and cut the extra suture tail after pushing the pre-tied knot.

The knot pusher and suture cutter may be used with any appropriate type of suture or material, including any appropriate size, length, and/or diameter of suture. Examples of suture materials may include: surgical-grade sutures such as catgut (plain, chromic), silk, polyglycolic acid, polylactic acid, polydioxanone, nylon, polypropylene, etc.

A pre-tied knot may refer to one or more knots formed in a length of suture. The pre-tied knot may be formed exclusively of suture material, or it may include one or more additional materials, and/or it may modify the suture material, or it may be formed of non-suture materials (such as metals, alloys, etc.). The pre-tied knot may be loose or taut and may be movable along a portion of the length of a suture. The knot body of the pre-tied knot may be formed of the same material as the suture on which the pre-tied knot is located, or it may be formed of a different material. The knot-body may also be tightenable. In some variations, the knot body is formed at the end of the length of suture from the end of the suture material. In some embodiments, the knot-body of the pre-tied suture typically may include one or more loops that may be cinched, tightened, and/or closed to complete the knot.

Another example of a knot pusher and suture cutter apparatus is shown in FIGS. 7A-9C. This example also includes a slideable inner member as described above for FIGS. 1A-6B. In addition, the variation shown in FIGS. 7A-9C includes a locking mechanism that prevents the inner member from moving when pushing the knot, preventing the suture for inadvertently releasing from the device.

Some variations of knot pusher and suture cutter (KPSC) devices may allow the suture to be unintentionally unloaded from the device while advancing knots into the tissue (e.g., in a knee joint). For example, an apparatus such as the one shown in FIGS. 1A-1B may include a bias that urges the inner mandrel in place distally, such as a compression spring. However, this compression spring may still allow a compressive force on the distal-facing end of the inner member (e.g., as applied by the knot of the suture) such that the inner mandrel is displaced slightly proximally, and the suture slides through the lateral slot (groove) in the outer holding tube. The force vector applied to the KPSC against the suture may include a component in the proximal direction of the long axis of the device.

Figure 7A:
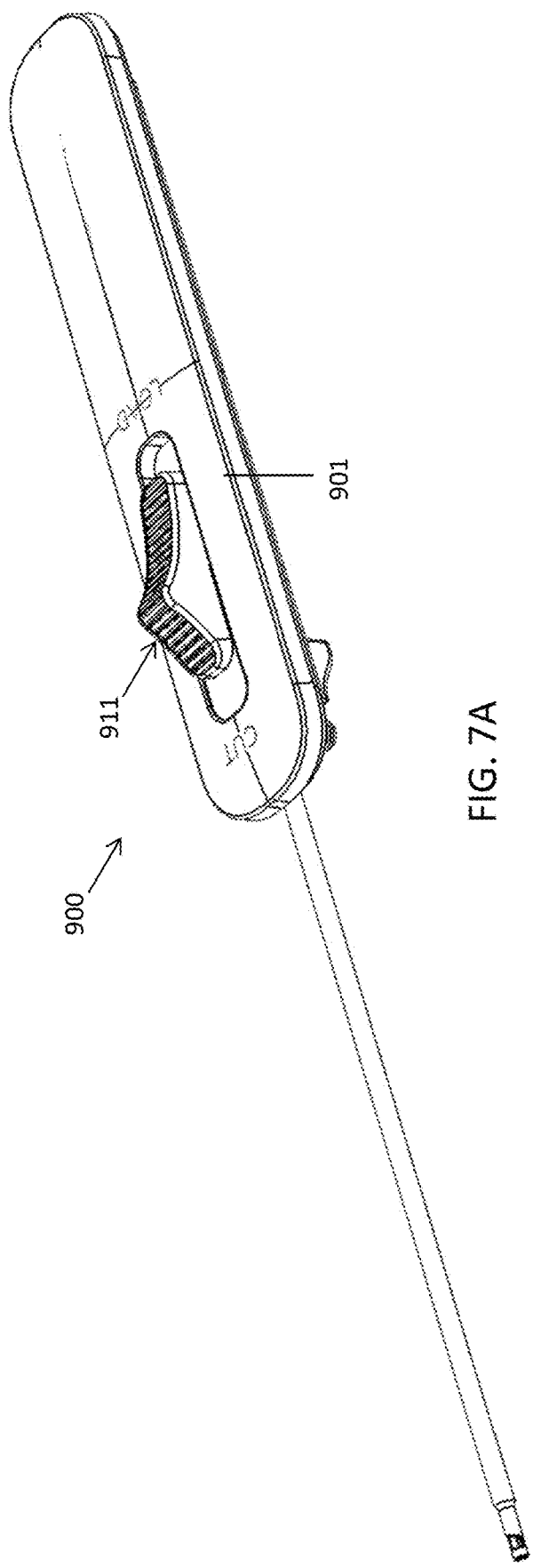
FIGS. 7A and 7B show top perspective and side views, respectively, of another variation of a knot pusher and cutter apparatus similar to the variation shown in FIG. 6A, above.
Figure 7B:
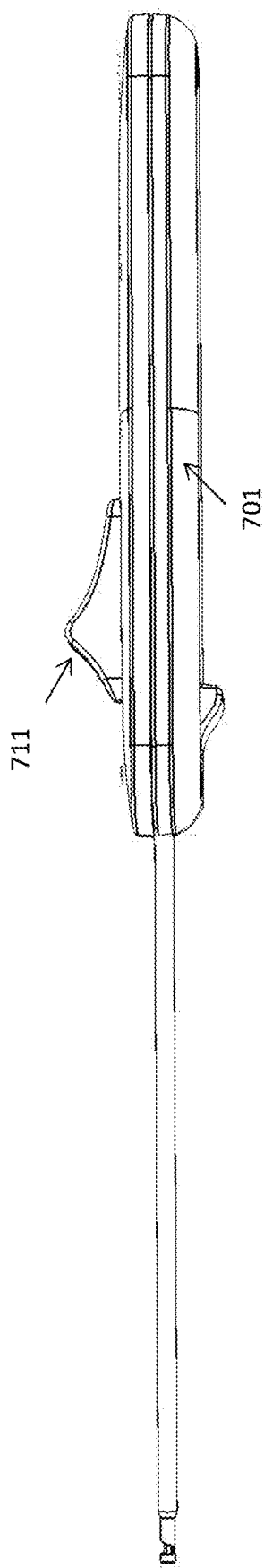

Thus, in the variation shown in FIGS. 7A-7B, the apparatus 900 includes an inner member (inner mandrel) that is sliceable in the long axis (distally and proximally) and has a lateral notched region. The device also includes an outer holding tube that includes a lateral slot (which may be J-shaped, L-shaped, or the like). As described above, the distal end of the device may be loaded with a suture length by sliding the inner member proximally (e.g., using the control 711 on the handle 901). The inner member may be biased (e.g., by a spring) so that it is at rest in a distal position. Further, the inner member may be locked by lock-out member (not visible in FIGS. 7A-7B) to prevent it from sliding distally against the bias and potentially releasing a suture held within the channel formed between the notched region of the inner member and the inner diameter of the outer holding tube. The lock may be configured so that it can be disengaged by activating a disengaging control or by applying a sufficiently large force (above a threshold locking force) to the inner member sliding control 911, or both.

Figure 9A:
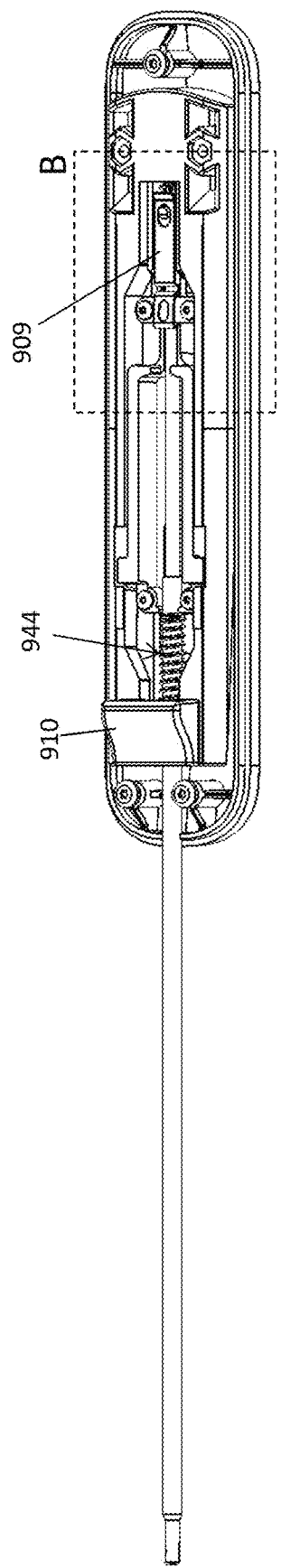
FIG. 9A shows the device of FIGS. 7A-8D with the bottom cover removed so that the lock out tab can be shown.
Figure 9C:
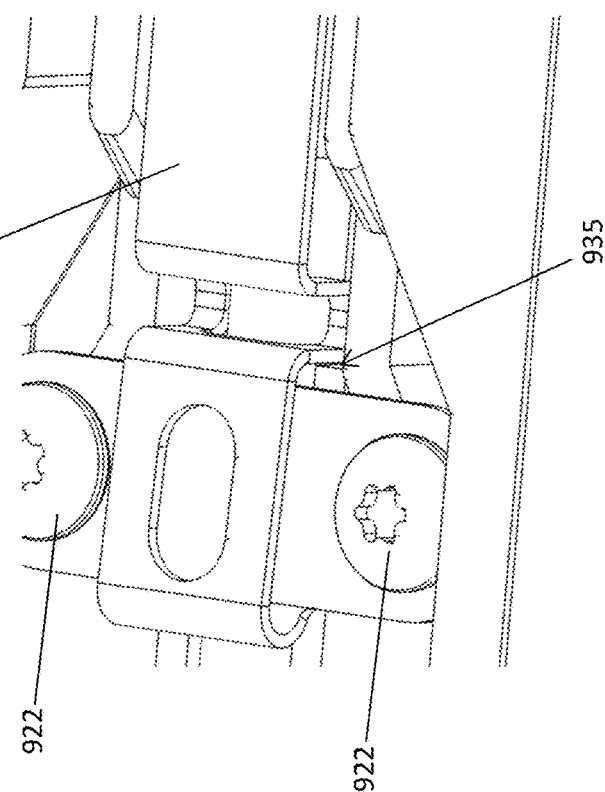
FIG. 9C is an enlarged view of the boxed region of the lock out tab shown in FIG. 9B.
Figure 9B:
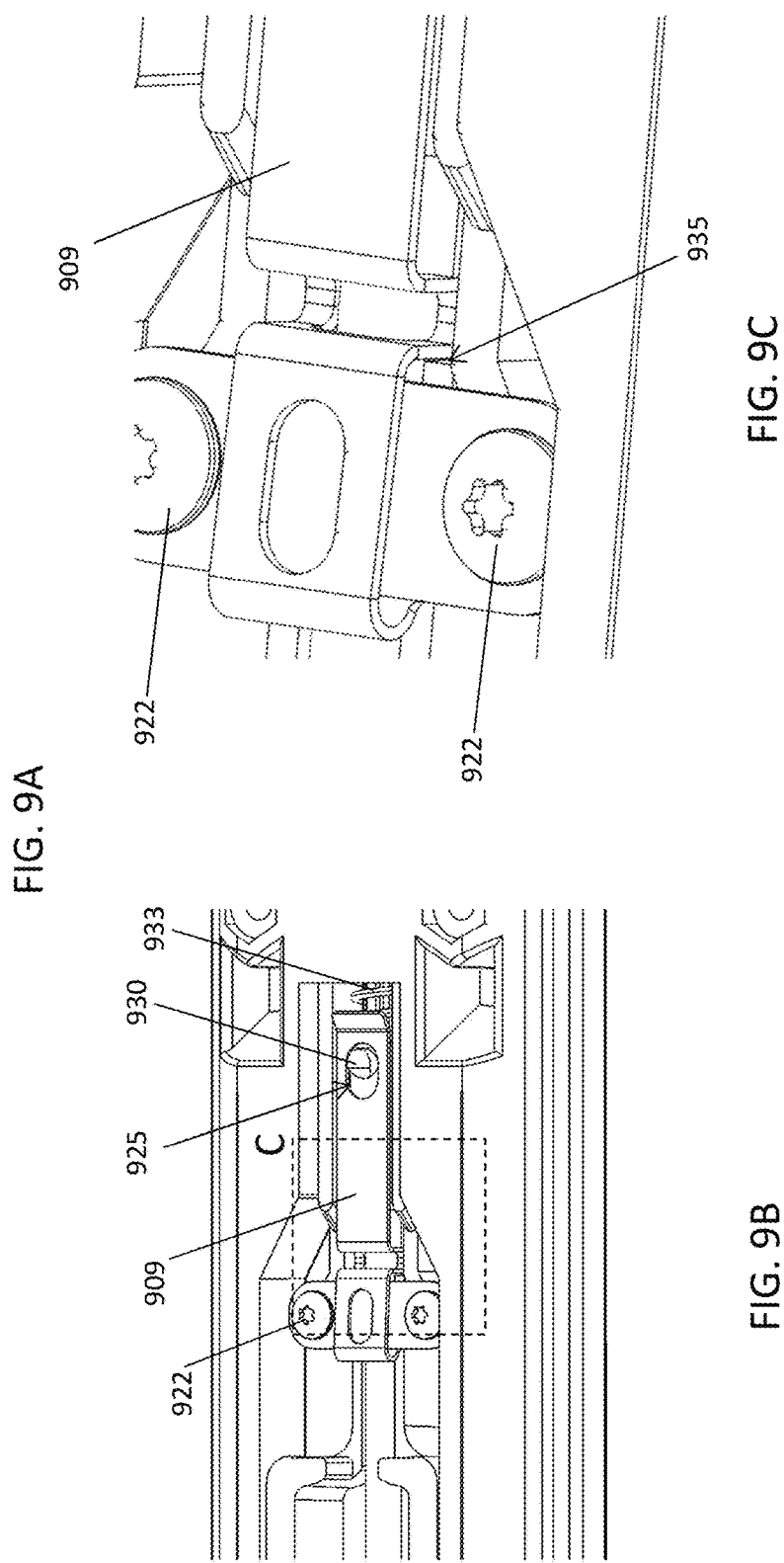
FIG. 9B shows an enlarged view of the boxed region B in FIG. 9A.
Figure 10A:
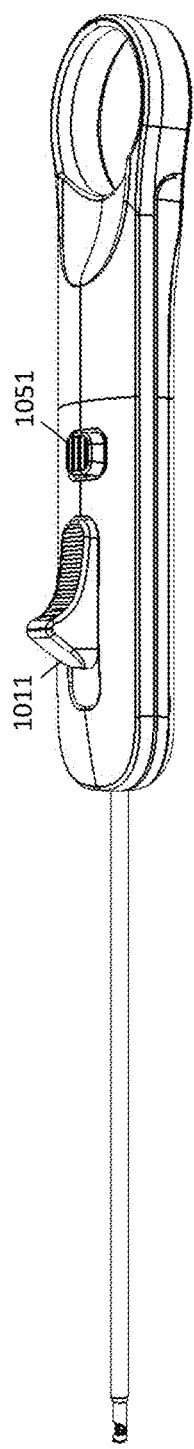
FIGS. 10A-10D show side perspective, top, side, and bottom views, respectively, of another variation of a knot pusher/cutter apparatus in which the inner member (mandrel) is rotatable and can be axially locked in a fixed position relative to the holding tube.
Figure 10B:
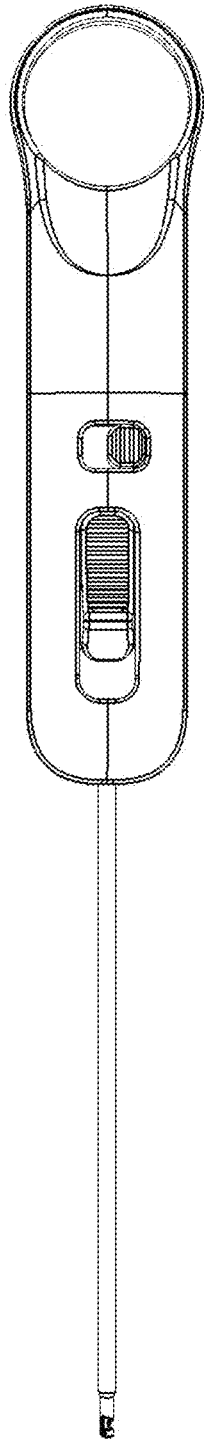
Figure 10C:
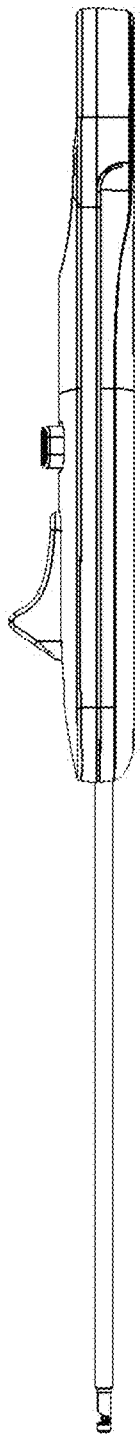
Figure 10D:
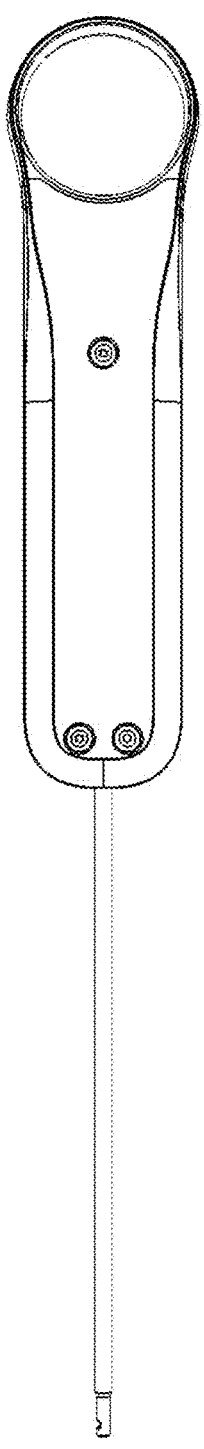

FIGS. 9A-9C illustrate one example of a lock out member that may be used to prevent the inadvertent sliding of the inner member and dropping of the suture. In FIG. 9A, for example, the bottom of the apparatus shown in FIGS. 7A and 7B is removed, showing the lock out mechanism (configured as a lock out tab) 909.

The lock-out tab 909 in this example is a sheet metal part that is affixed (e.g., screwed 922) to the upper housing of the handle. The proximal end of the lock-out tab includes a hole 925 that surrounds a boss feature 930 on the inner member holder. The inner member holder is rigidly attached to the inner mandrel (inner member). The bias 933 for the inner member (compression spring) is located proximal to the locking member, and urges the inner member distally. If a compressive force is applied to the mandrel, for example, by a knot at the mandrel's distal end, the mandrel and the attached mandrel holder will move proximally only until the boss 930 feature on the mandrel holder reaches the end of the lock-out tab slot 925 in which it resides, limiting the axial movement of the inner member. Limiting the axial movement of the mandrel in this manner prevents the suture from prematurely unloading from the distal end of the apparatus.

In operation, the lock-out tab may arrest the proximal movement of the mandrel unless it is intentionally disengaged. For example, the lock-out member may be disengaged when the user actuates the slider. In FIG. 9C, a sharp corner feature 935 on the slider may push against a bend in the lock-out tab. As the user retracts the control (e.g., slider 711) in preparation for loading the suture into the device, the lock-out element may bend (e.g., by deflecting or hinging) upwards, until the arresting slot 925 no longer resides around the boss feature 930 on the mandrel holder. The slider is now free to push the mandrel holder, and mandrel, proximally and compress the compression spring 933, pulling the inner mandrel proximally and opening the channel in the distal end to allow loading of the suture.

In FIGS. 9A-9C, other elements of the apparatus are also visible, including the cutter lock 910, and bias (compression spring 944).

Figure 8A:
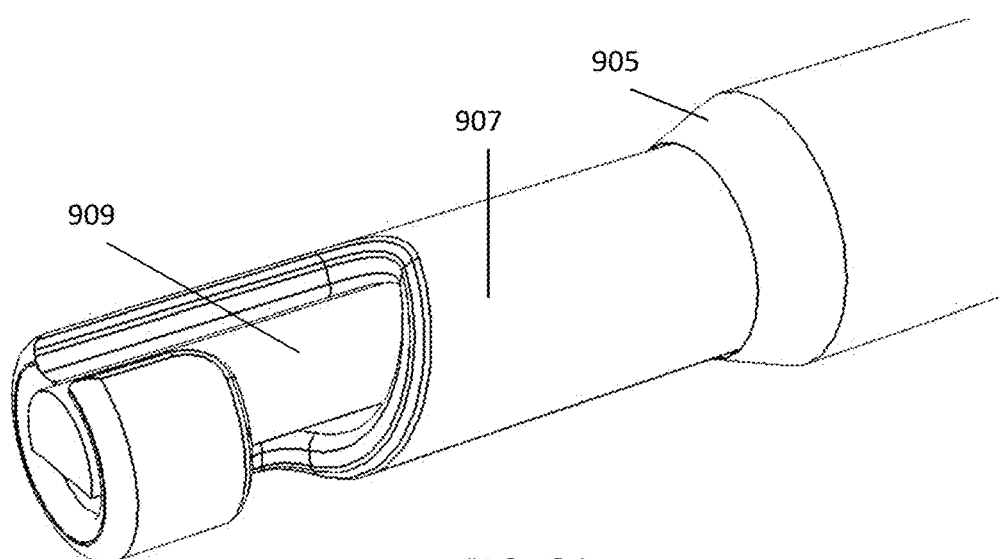
FIGS. 8A-8E illustrate the operation of the distal end of the apparatus of FIGS. 7A-7B.
Figure 8B:
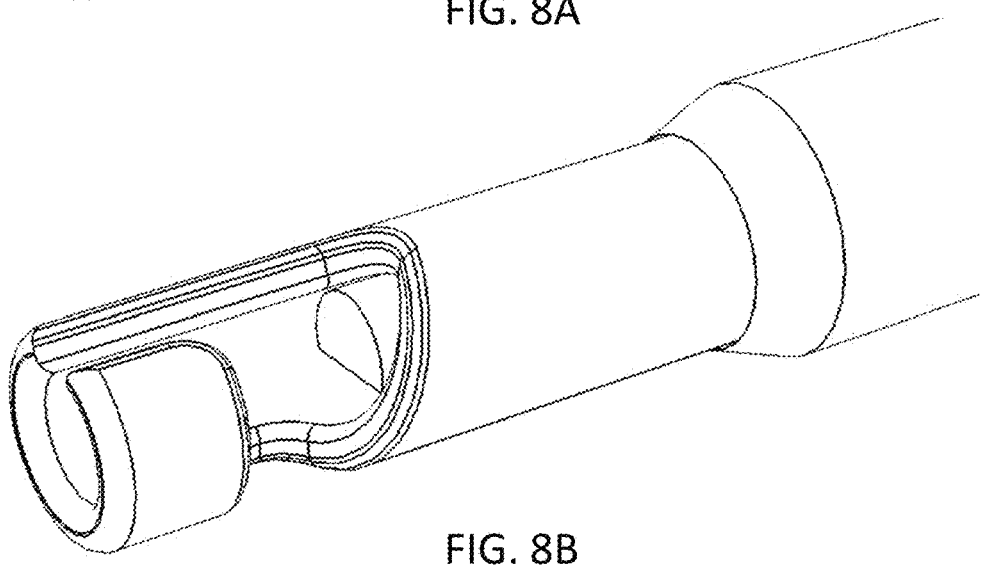

FIGS. 8A-8F illustrate operation of the apparatus shown in FIGS. 7-7B and 9A-9C. In this example, the distal end of the apparatus is shown, including the outer holding tube 907 and the inner member (inner mandrel 909). In FIG. 8A the inner member 909 is shown at rest, biased distally by the compression spring so that the distal end of the inner membrane is flush (or approximately flush) with the distal end of the outer holding tube 907. The inner member may be locked by the locking mechanism (lock out tab, not visible in FIG. 8A). To load a suture, the inner member may first be axially slid proximally, as shown in FIG. 8B. In this example, the control on the handle may first be moved to first disengage the lock out tab, and after it has disengaged, to slide the inner member proximally. Alternatively a separate control may be used to disengage the lock out mechanism, for example, a button that deflects the lock out mechanism so that it does not secure to the inner member (e.g., releasing a boss, as described in FIGS. 9A-9C, above).

Figure 8C:
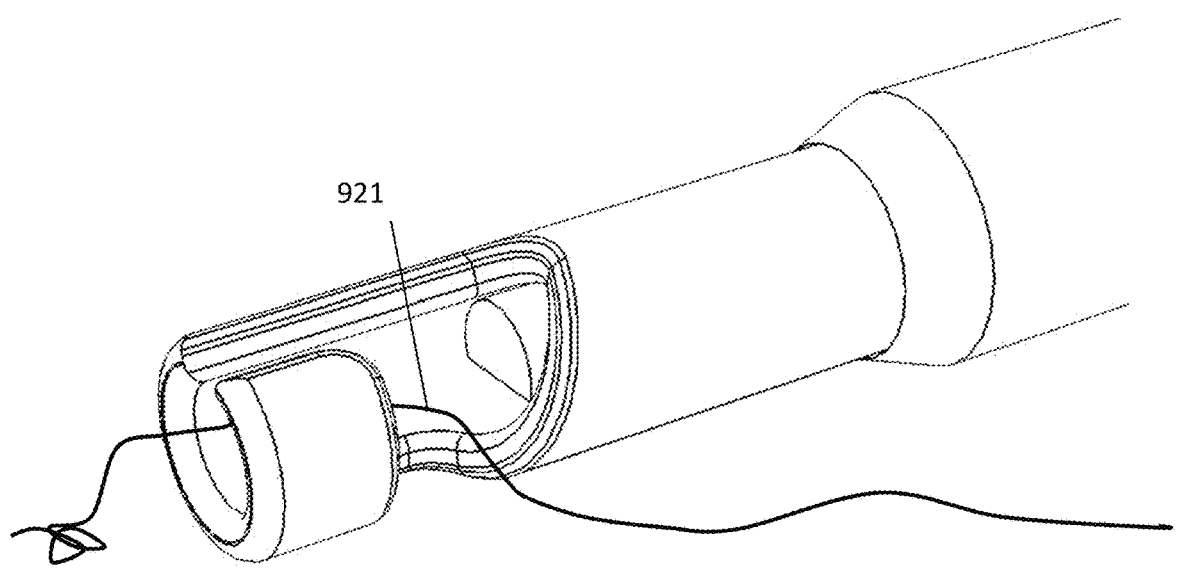
Figure 8D:
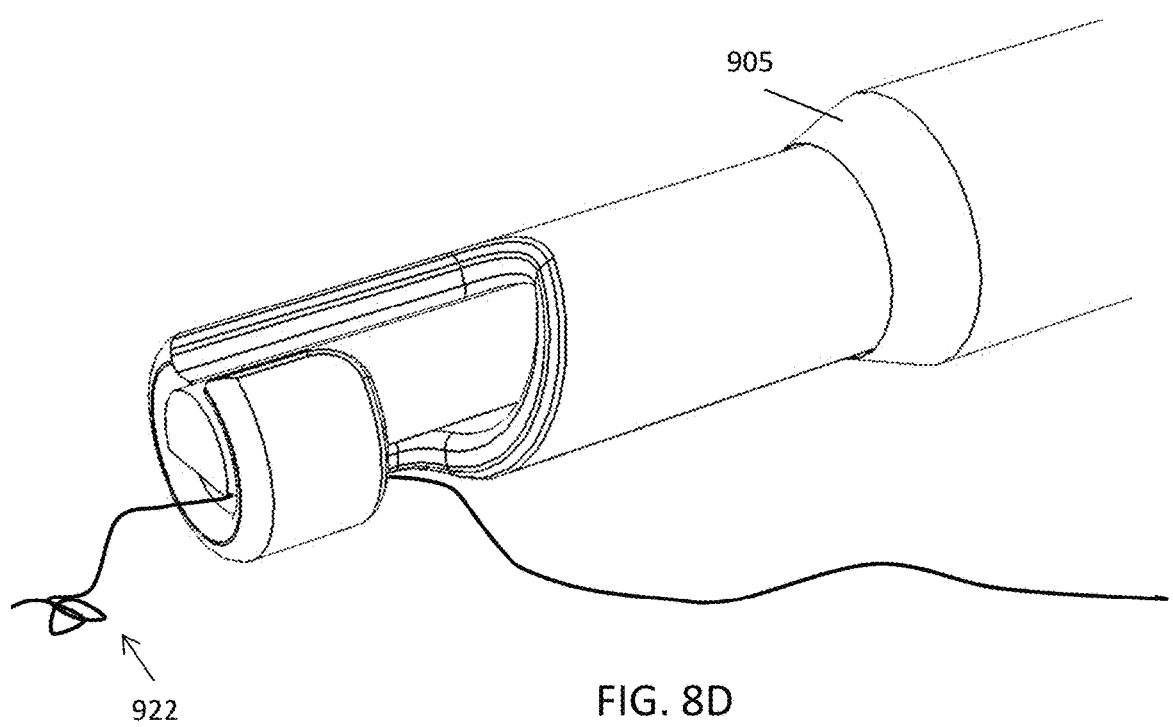
Figure 8E:
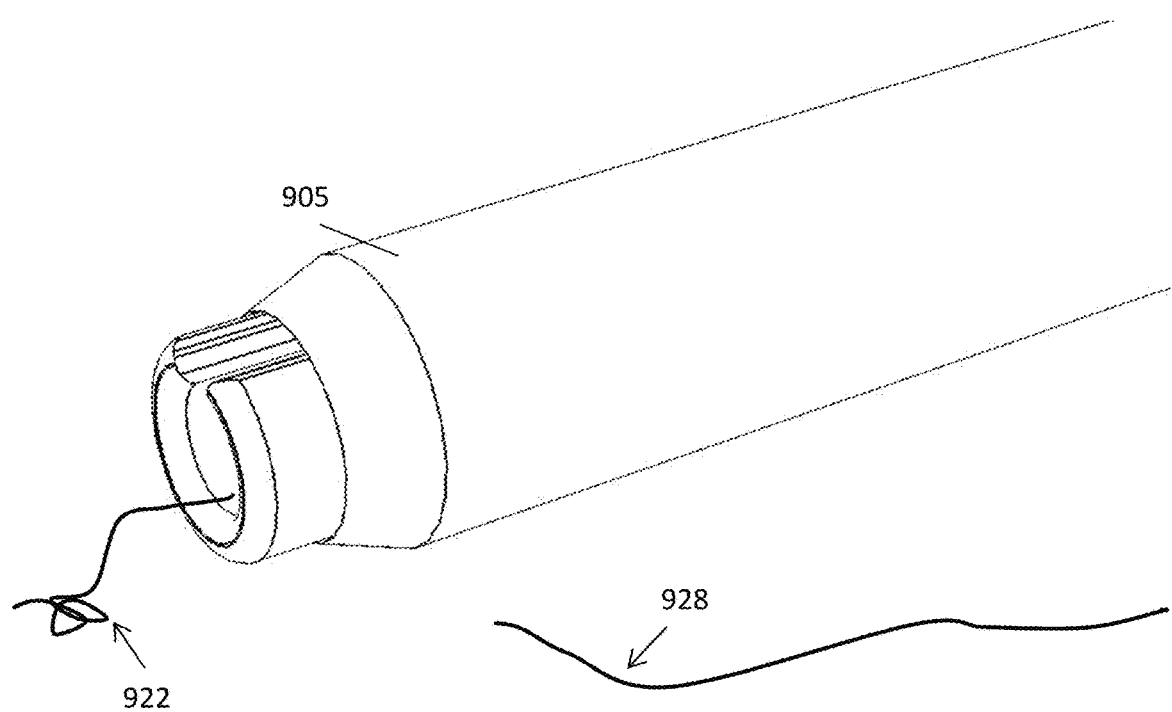

As shown in FIGS. 8C and 8D, the suture 921 may then be loaded through the lateral slot into the inner chamber of the outer holding tube, and the inner member released (e.g., by releasing the control) so that it returns to a distal position, with the suture trapped in a channel 955, between the inner member and the outer holding tube, as shown in FIG. 8D. The device may then be used to push the knot 922 distally; once positioned, the outer cutter 905 may be actuated (e.g., by releasing the lock and operating the control to cut the suture), cutting the proximal length 928 of suture from the region immediately adjacent to the knot 922, as illustrated in FIGS. 8D and 8E.

Another variation of a knot pusher and suture cutter apparatus is shown in FIGS. 10A-11F. In this example, the inner member (mandrel) rotates relative to the outer holding member, allowing loading of a suture length into the distal end of the device. In this variation, the handle 1001 includes an inner member control 1051 that rotates the inner member and a separate control 1011 that controls the cutter; a separate lock for the cutter (not shown) may also be included as described above. In some variations the inner member control and the cutter control may be part of the same control, as described above (where sliding one direction rotates the inner member for loading, and sliding in the other direction drives the cutter for cutting). In the variation shown in FIGS. 10A-10D, the proximal end of the device also include a thumb ring 1080 that may be used to hold and manipulate the apparatus.

This variation may provide another mechanism that prevents inadvertent release of the suture from the distal end of the device. In this example, the mandrel may be rotated while held at the distal position. A notched region on the inner member (mandrel) provides sufficient room for loading a suture, as illustrated in FIGS. 11A-11F. In this example, the notched region of the mandrel is a flat on the mandrel which creates enough space for a suture between the inner wall of the outer holding tube, but not enough so that the knot can pass through this channel, as shown in FIG. 11E. If the mandrel is rotated 180 degrees, the space for the suture to reside is adjacent to the slot on the cutter guide as shown.

Figure 11A:
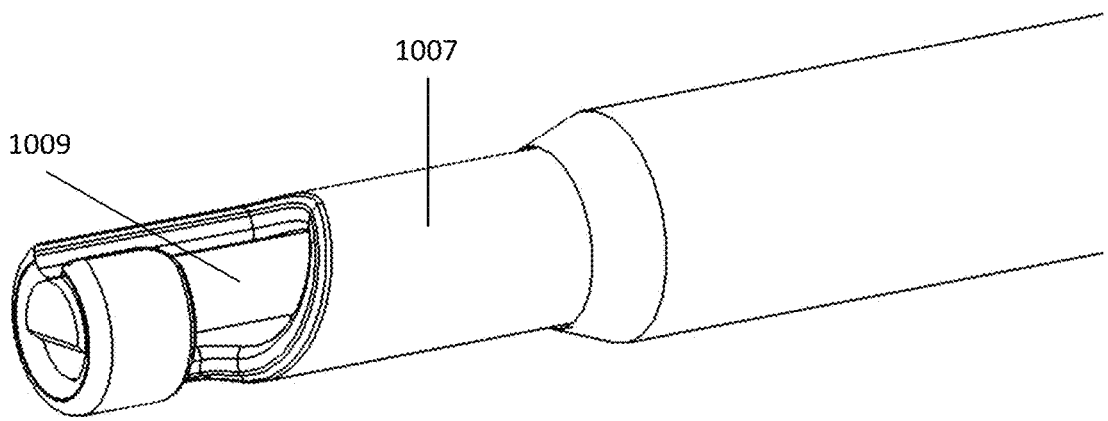
FIGS. 11A-11F illustrate the operation of the apparatus shown in FIGS. 10A-10D.
Figure 11B:
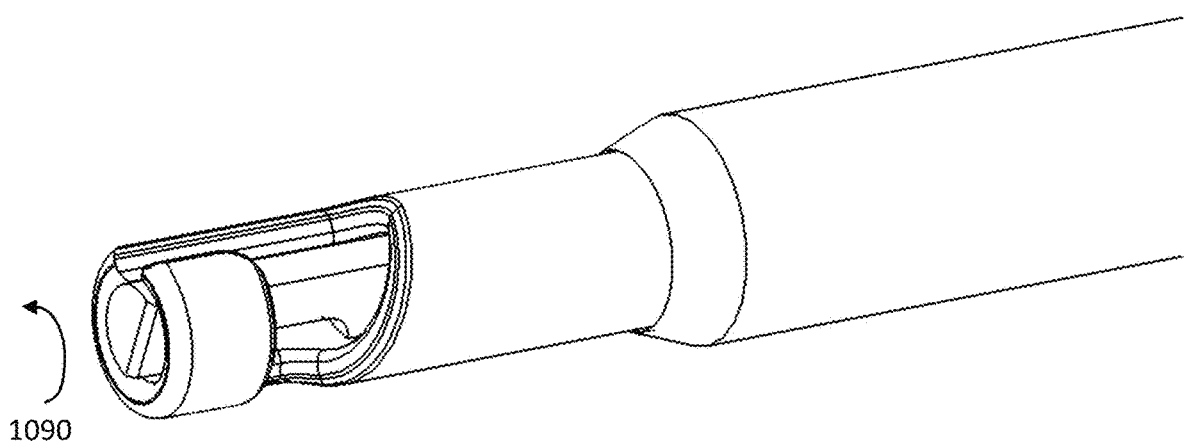
Figure 11C:
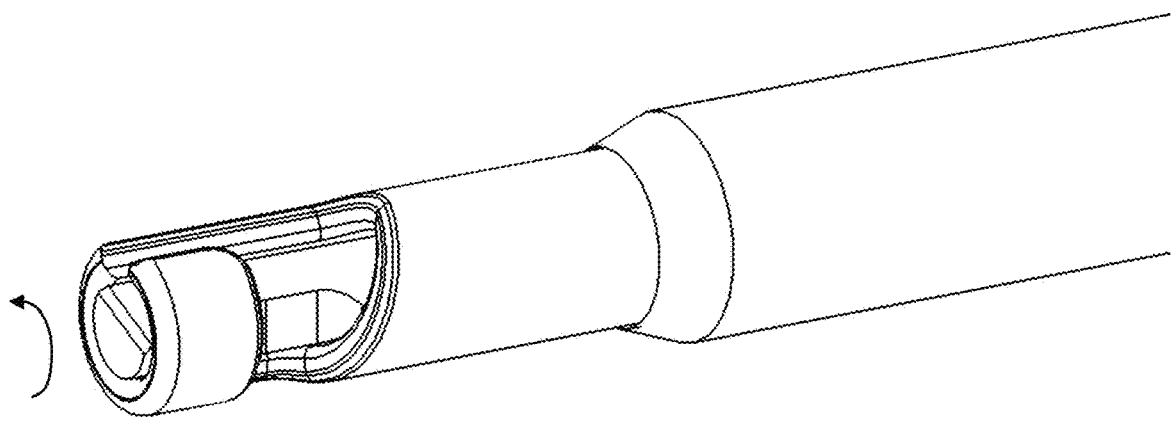
Figure 11D:
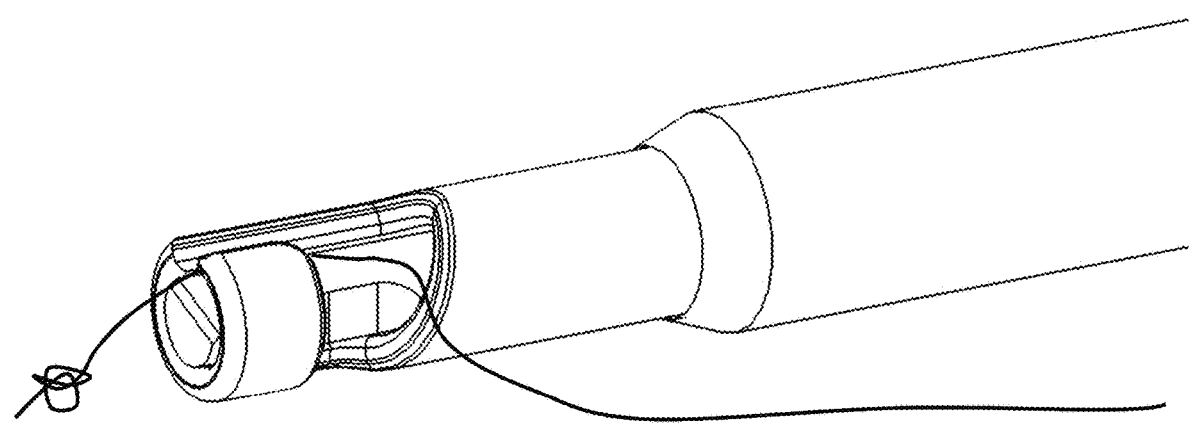
Figure 11E:
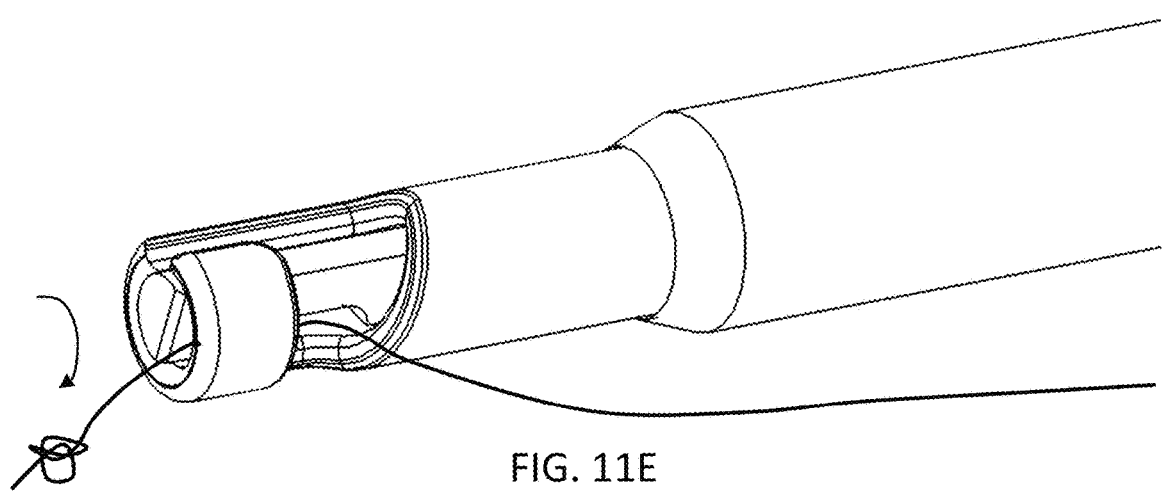
Figure 11F:
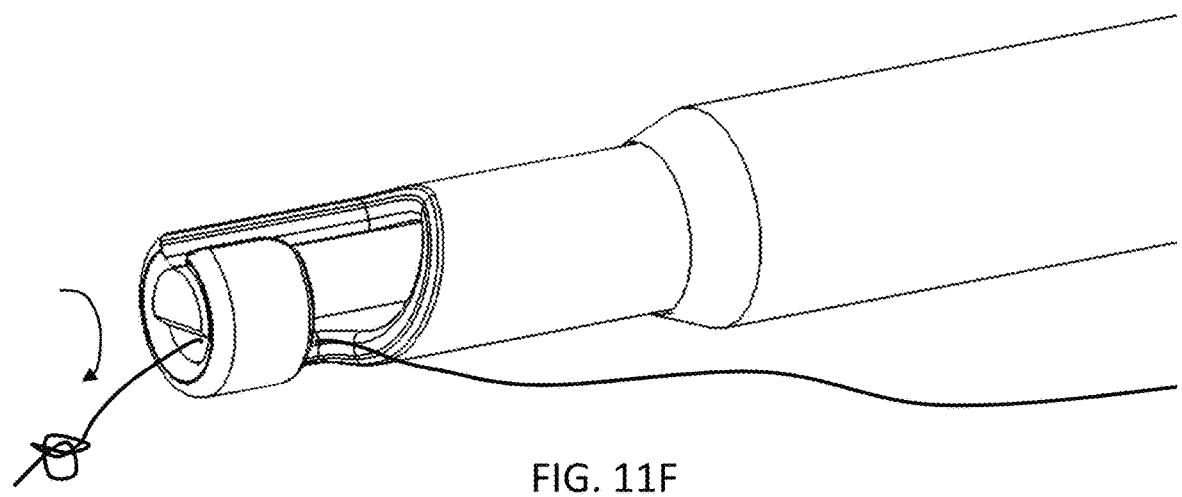

For example, in FIG. 11A, the rest position shown the inner member 1009 rotated with the notched (cut-out) region 1013 opposite the lateral slot through the outer housing tube 1007. The inner member may be rotated 1090 (e.g., by actuating the control 1051 on the handle of the device), as shown in FIG. 11B, until the notch is aligned with the lateral slot, as shown in FIG. 11C. Thereafter, a length of suture 1121 may be inserted into the notch, and the inner member released back to the closed position (or actively closes), so that it rotates back away from the lateral slot in the outer housing tube, as shown in FIGS. 11E and 11F. As mentioned above, the rotatable inner member may also be biased in the 'closed' position (e.g., rotated away from the lateral slot and/or may be locked in this closed position, preventing inadvertent rotation, e.g., using a locking mechanism such as a pin, clamp, lock out element, or the like.

Figure 13A:
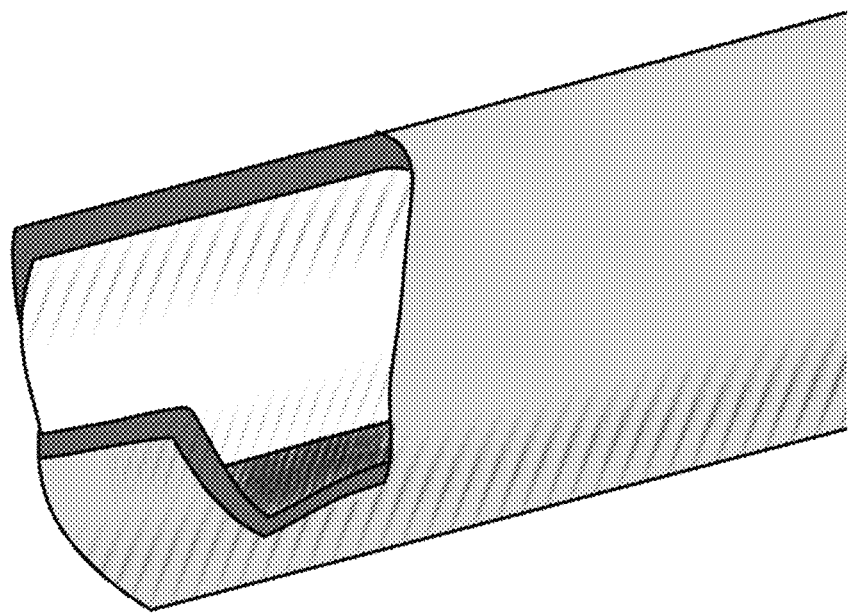
FIGS. 13A-13D illustrate operation of another example of an apparatus having a rotatable inner member.
Figure 13B:
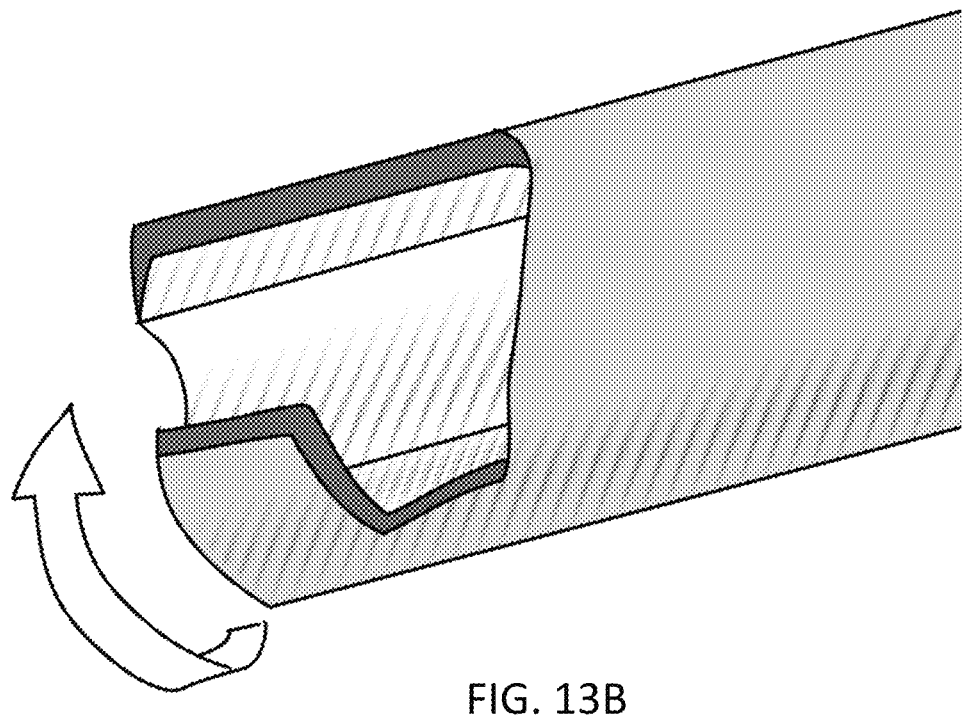
Figure 13C:
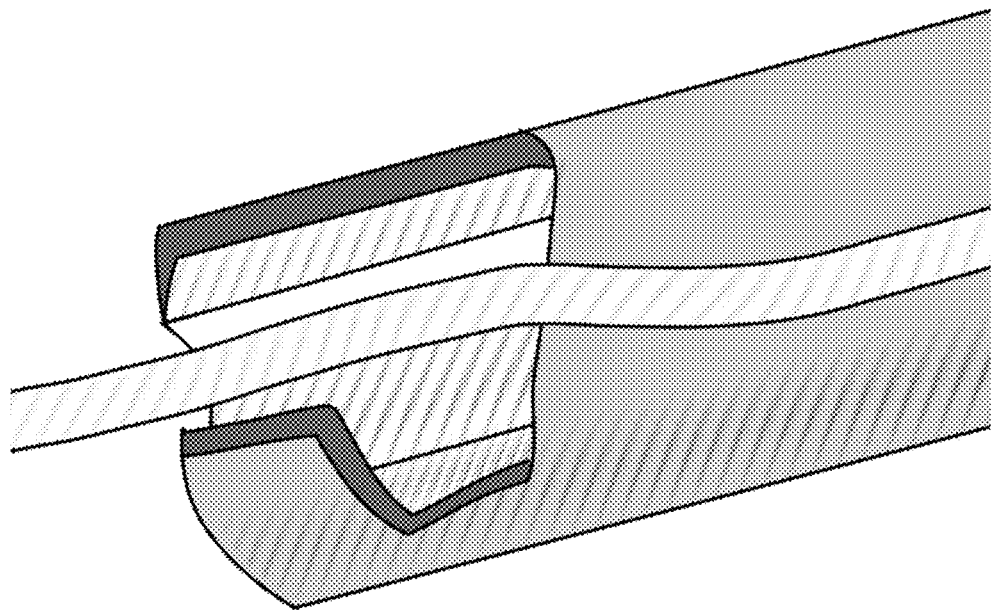
Figure 13D:
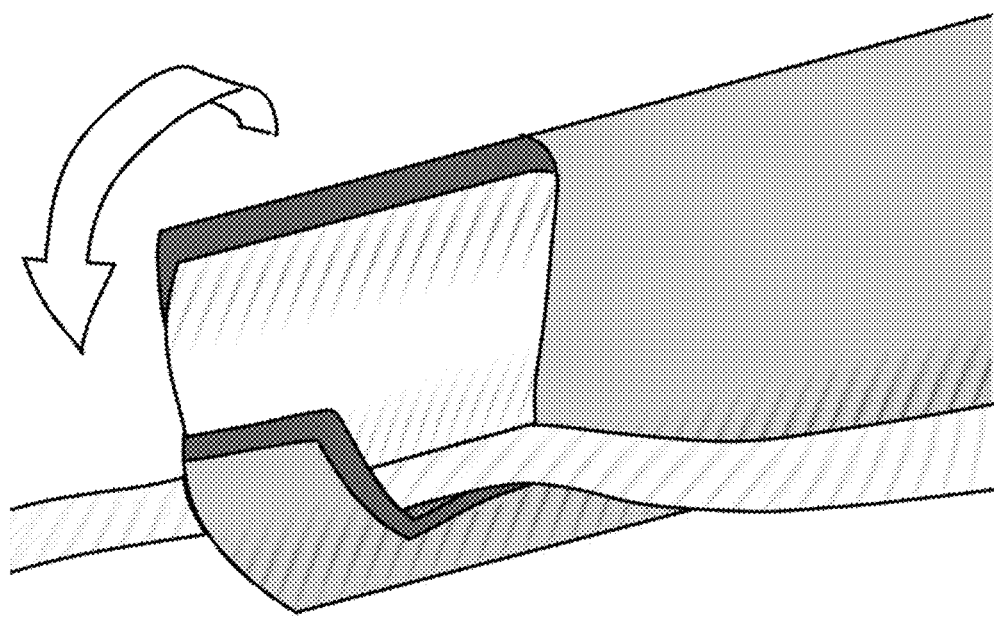
Figure 14A:
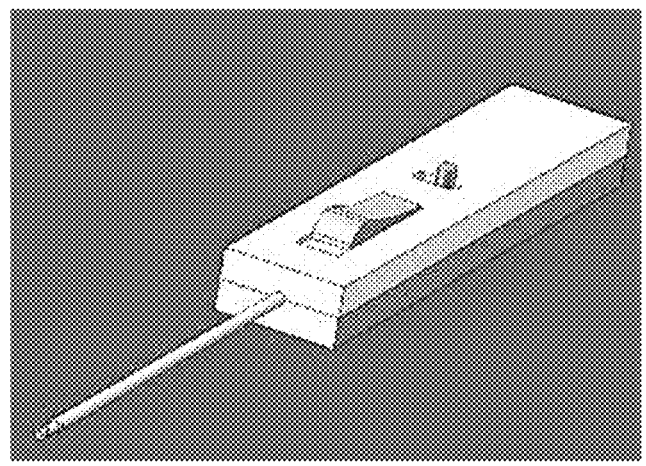
FIG. 14A shows one example of an apparatus such as the one shown in FIGS. 10A-11F, including a control for rotating the inner member.
Figure 14B:
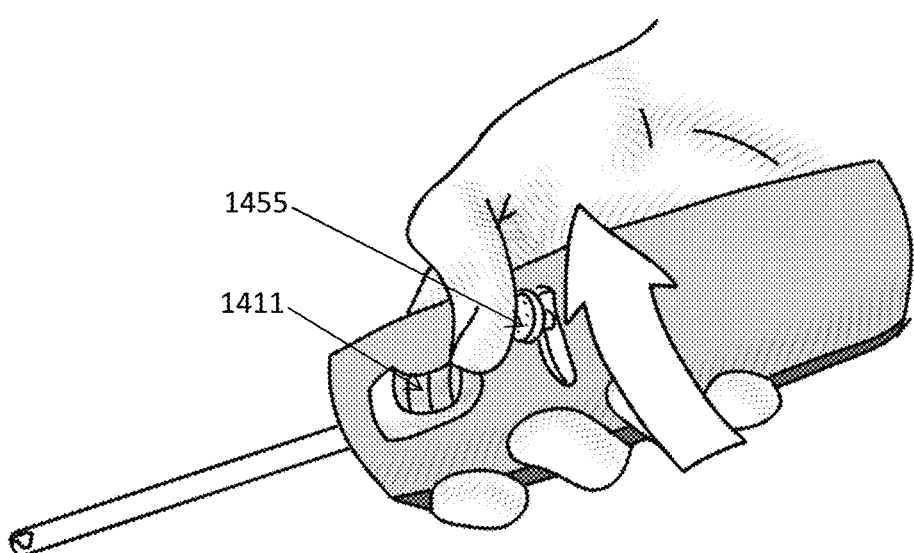
FIGS. 14B and 14C illustrate operation of the apparatus shown in FIG. 14A.
Figure 14C:
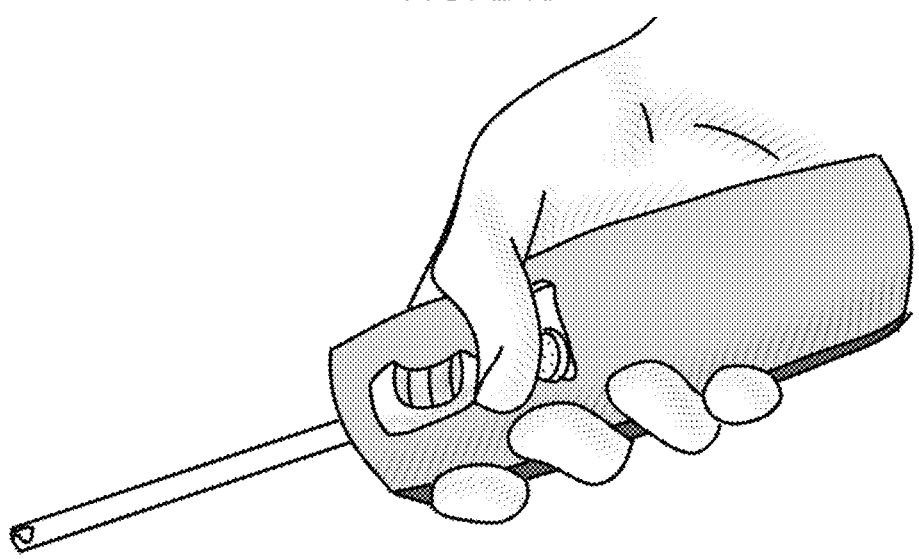

Another variation of a knot pusher and suture cutter apparatus is shown in FIGS. 14A-14C. This example, similar to that shown in FIGS. 10A-11F also includes a rotatable inner member. FIGS. 14B and 14C illustrate operating of the inner member rotation control 1455. This variation of a control is shown as a slider, and sliding the slider causes rotation of the inner member. In this example, a separate control (slider 1411) may be connected to the cutter tube to facilitate moving the cutter tube distally along the devices axis. The inner member control 1455 may drive the rotation of the inner member as it is moved side-to-side, as shown. The side to side motion may be translated by a rack gear within the handle. The rack may interact with a pinion gear attached to the mandrel. By moving the inner member control side-to-side, the user may toggle the mandrel's angular orientation between a loadable configuration (see FIG. 13B) and a loaded configuration (See FIG. 13D). The device may also include features (e.g., on the handle) to fix the mandrel's axial position, which further mitigates any chance of premature unloading, and allow for changes in angular position. FIGS. 13A-13D illustrate loading of the apparatus of FIGS. 14A-14C with a suture, starting from an at-rest initial configuration as shown in FIG. 13A, rotating the inner member to expose the channel within the outer housing tube and the inner member (FIG. 13B), placing the suture within the channel through the lateral slot (FIG. 13C) and locking the suture length within the distal end by rotating the inner member back away from the lateral slot (FIG. 13D). The inner member in FIGS. 14A-13D is a tube having a notched distal end removing a portion of the tube wall, as apparent in FIGS. 13B and 13C, wherein the inner member notch is visible through the lateral slot.

In any of the variations of devices described above, the apparatus may include an inner member that is elongate and fits within the outer housing tube. In some variations the inner member/inner mandrel is an elongate cylindrical member. The cylinder may be solid or hollow, and may have a generally circular, oval, rectangular, triangular, or other cross-section. At least the distal end of the inner member may include a cut-out or notch region; in some variations the majority of the length of the inner member may include a notch region. For example, the inner member may be a split cylinder. In some variations the notch region may be a compound notch, in which the first notch region extends from the distal end towards the proximal end, and a second notch region intersecting with and at an angle with the first notch region begins proximal to the distal end. A compound notch may allow a guide or surface for the suture that may help steer the suture to exit the lateral slot in a particular location.

Figure 12A:
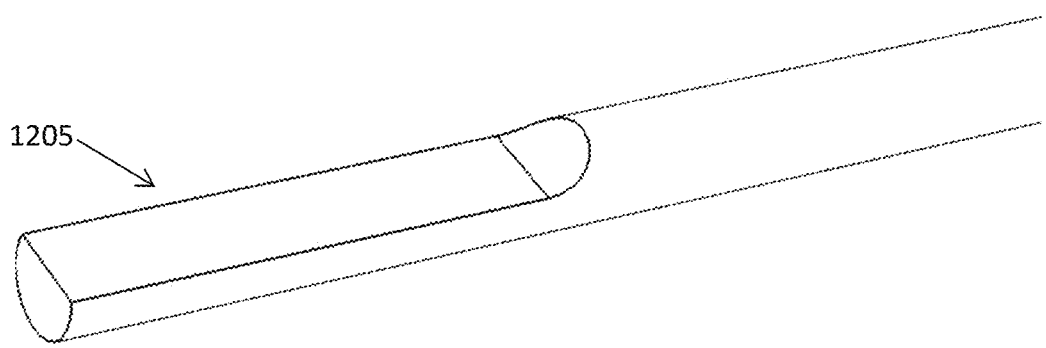
FIGS. 12A-12C show variations distal ends of inner members that may be used with any of the apparatuses described herein.
Figure 12B:
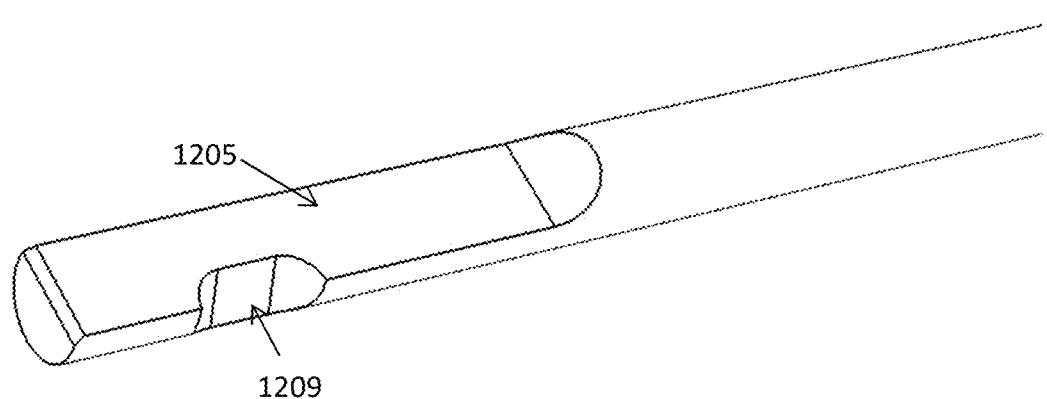
Figure 12C:
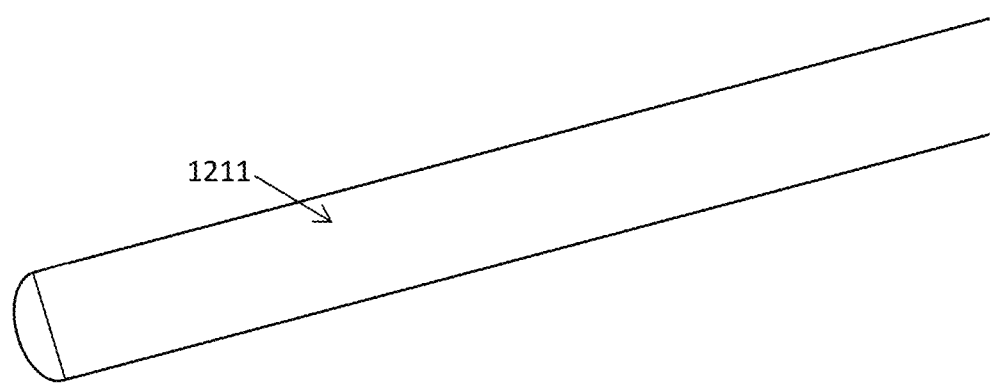

For example, FIGS. 12A-12C illustrate variations of inner members that may be used in any of the variations described herein. In FIG. 12A, the inner member is a cylinder having a generally round profile with the distal end notched to provide a cut-out region 1205. This variation of inner member is shown in FIGS. 7A-9C. FIG. 12B is another example of an inner member/inner mandrel in which a distal compound notch is used; the cut-out region forms a first notch region 1205' and a second notch region 1209. This variation is used in FIGS. 10A-11F. FIG. 12C is another variation of an inner member in which the mandrel is notched over much of the length of the inner member, so that the inner member includes a substantially flat side 1211.

Figure 15A:
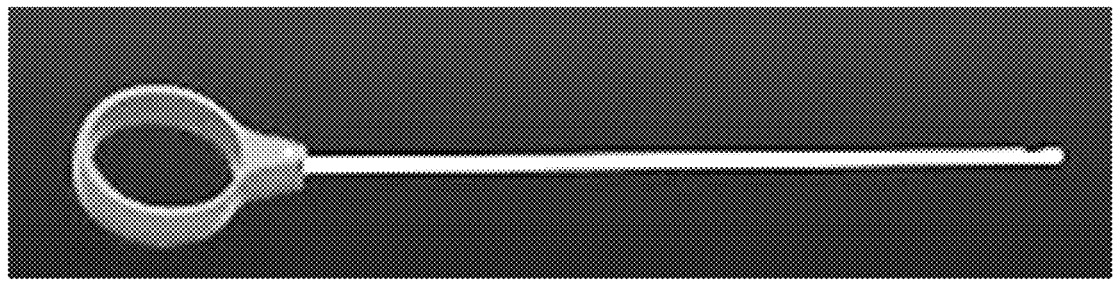
FIGS. 15A and 15B illustrate thumb rings that may be included as the proximal end of any of the devices described herein.
Figure 15B:
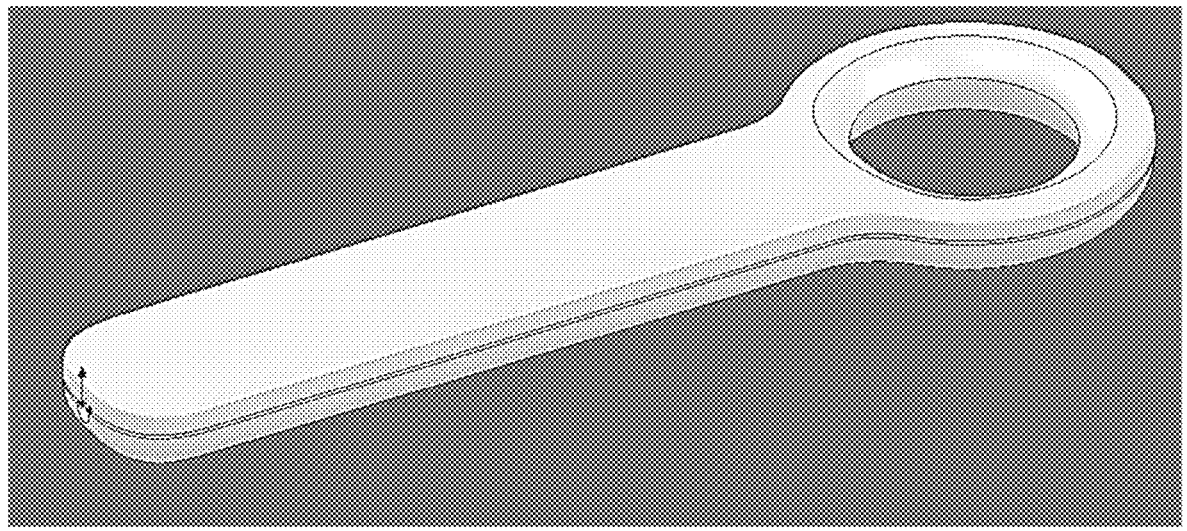

As mentioned above, any of the apparatuses described herein may include a proximal thumb ring, as shown in FIGS. 10A-10D. FIGS. 15A and 15B illustrate other variations of thumb rings. When a surgeon uses a thumb ring, they often rotate between multiple angular orientations. Because the apparatuses described above are configured to prevent prematurely unloading of the suture from the distal end of the device, even at angular orientations in which the suture is lined up with the cutter guide slot and force is applied by the knot to drive the inner member away from the lateral slot, a thumb ring may be used. Thus, a thumb ring may be added to the apparatus because there is little risk of prematurely unloading the suture. The exemplary thumb rings shown in FIGS. 15A and 15B do not show other handle features that may be included, including any of those shown above in FIGS. 1A-1B, 7A-7B and 10A-10D.

Figure 16A:
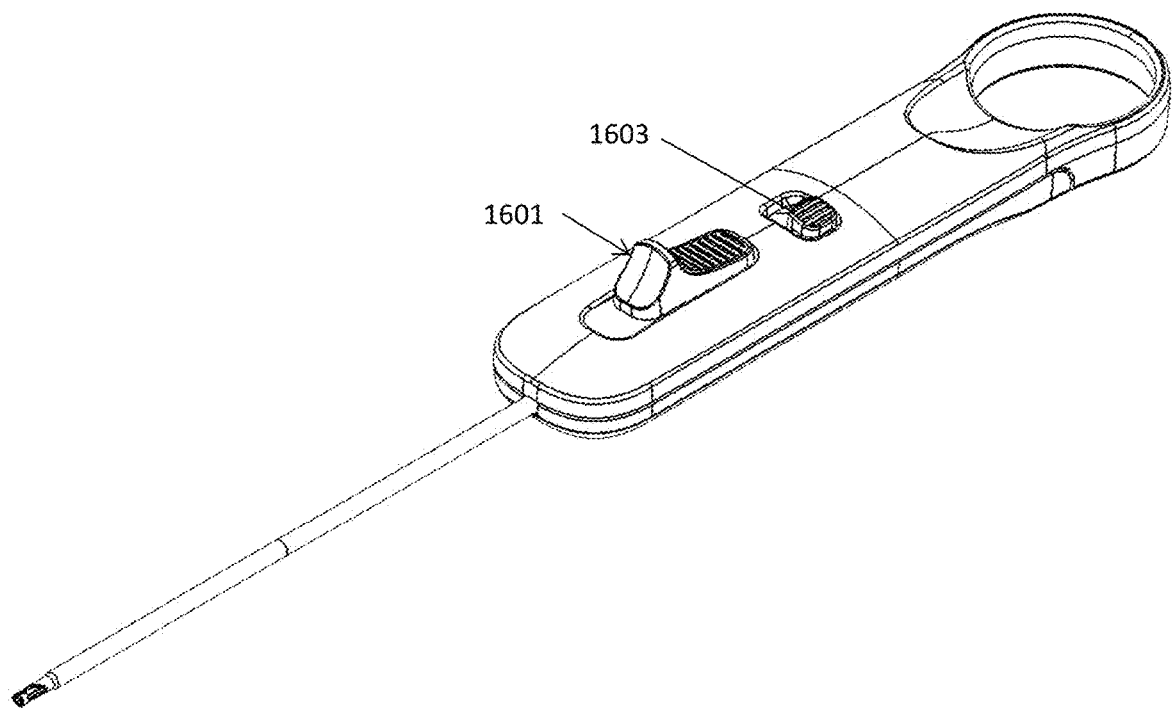
FIG. 16A shows another variation of a knot pusher and suture cutter apparatus (similar to that shown in FIG. 1A) in front perspective view, with the inner mandrel in a relaxed (configuration).
Figure 16B:
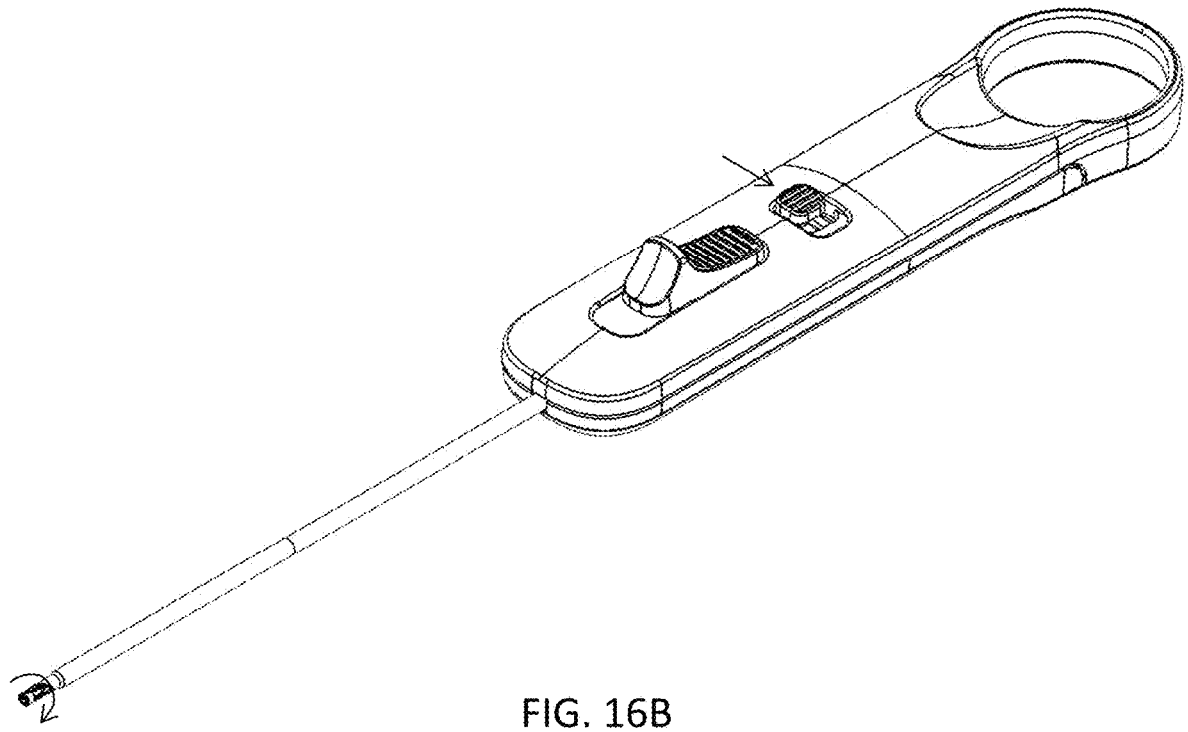
FIG. 16B shows the apparatus of FIG. 16A with the inner mandrel rotated by actuation of a control on the handle of the device so that a suture may be loaded into the distal end.
Figure 16C:
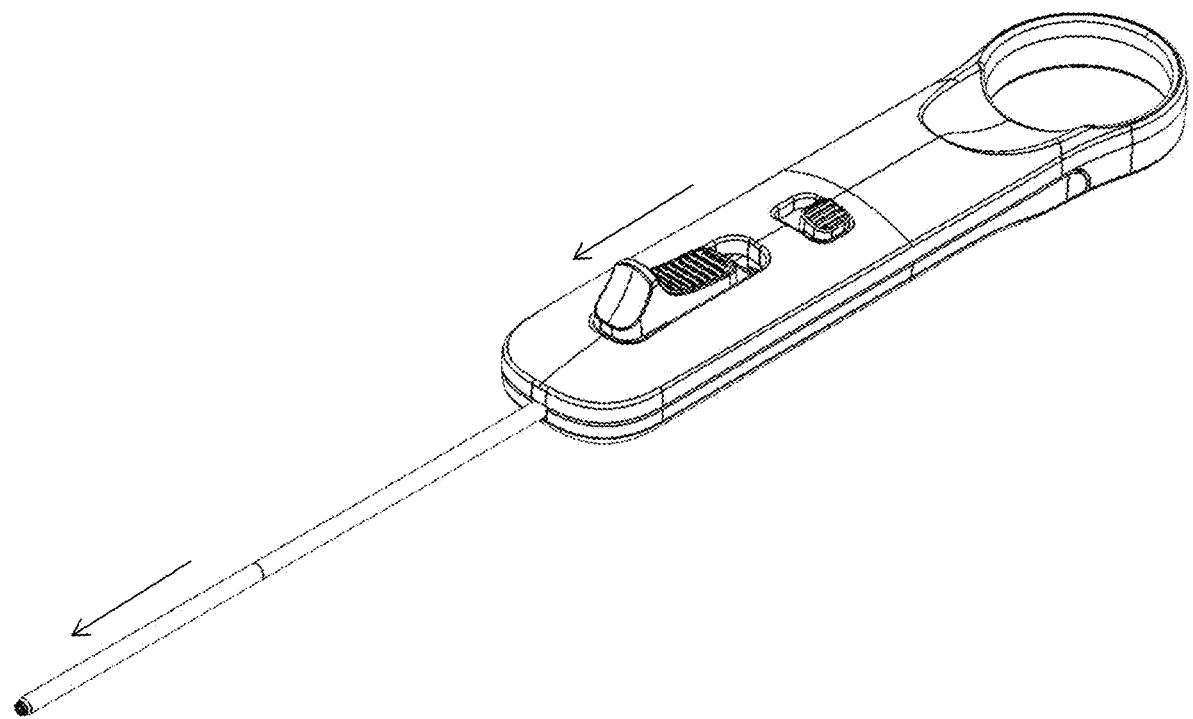
FIG. 16C shows the apparatus of FIG. 16A actuated by pushing a cutter control on the handle to actuate cutting of the suture held in the distal end of the device.
Figure 17A:
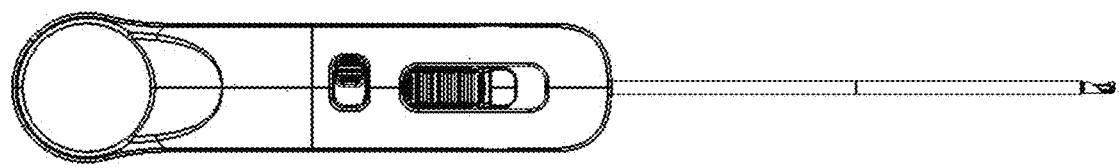
FIG. 17A shows a top view of the knot pusher and suture cutter apparatus of FIG. 16A.
Figure 17B:
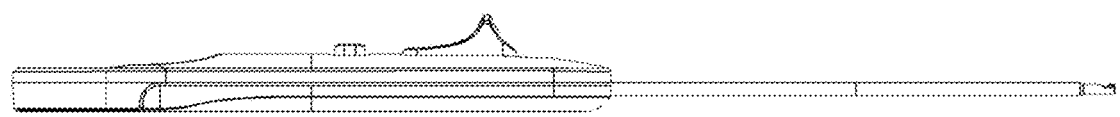
FIGS. 17B and 17C show left and right side views, respectively of the knot pusher and suture cutter apparatus of FIG. 17A.
Figure 17C:
Figure 18A:
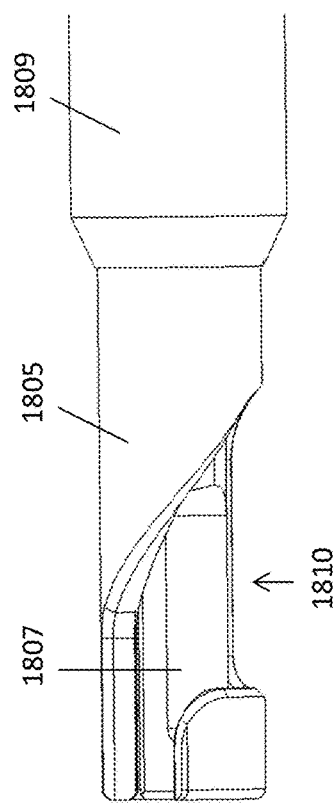
FIGS. 18A and 18B show top and top perspective views, respectively, of the distal end of a knot pusher such as the one shown in FIG. 17A with the mandrel rotated to allow loading and unloading of a suture (e.g., knotted suture) into the distal end.
Figure 18B:
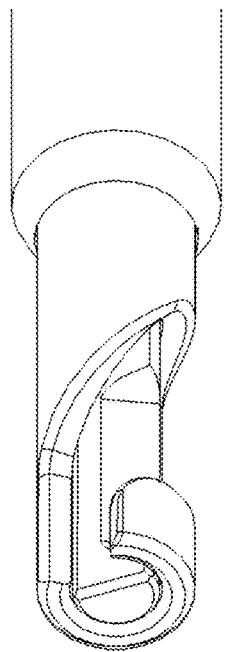
Figure 18C:
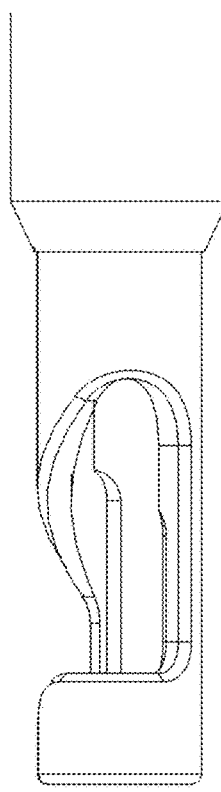
FIGS. 18C and 18D show side and side perspective views, respectively of the distal end knot pusher and suture cutter shown in FIGS. 18A and 18B.
Figure 18D:
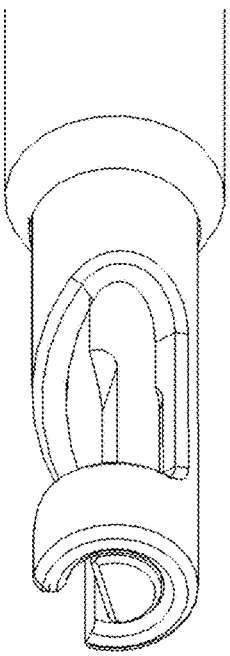
Figure 18E:
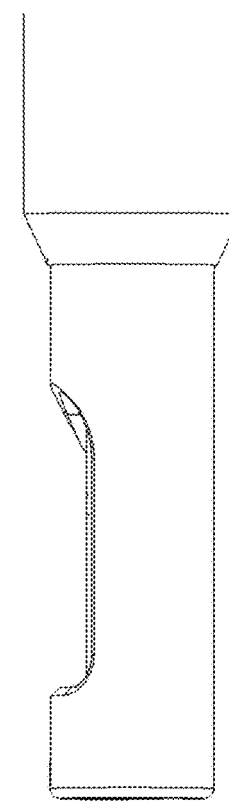
FIGS. 18E and 18F show bottom and bottom side views, respectively, of the distal end knot pusher and suture cutter shown in FIGS. 18A and 18B.
Figure 18F:
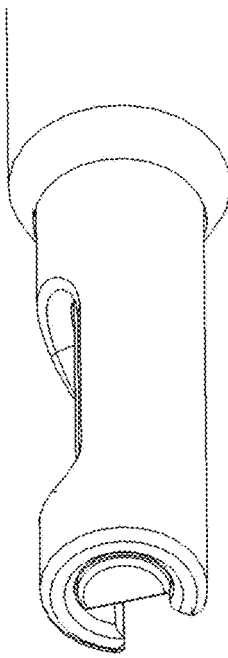
Figure 19A:
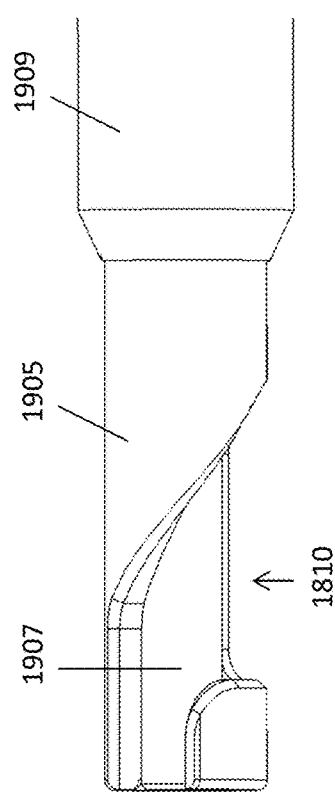
FIGS. 19A and 19B show top and top perspective views, respectively, of the distal end of a knot pusher such as the one shown in FIG. 17A with the mandrel rotated to prevent loading and unloading of a suture (e.g., knotted suture) into the distal end.
Figure 19B:
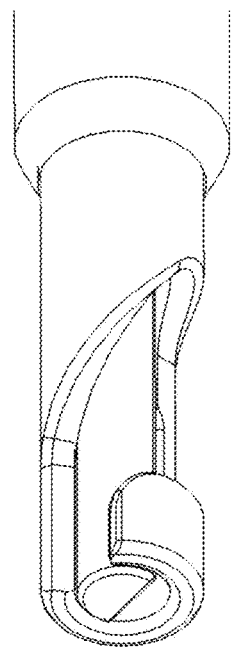
Figure 19C:
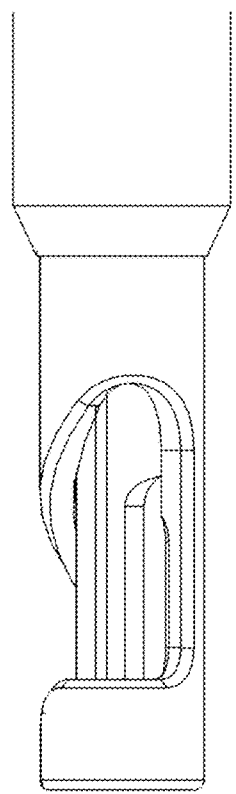
FIGS. 19C and 19D show side and side perspective views, respectively of the distal end knot pusher and suture cutter shown in FIGS. 19A and 19B.
Figure 19D:
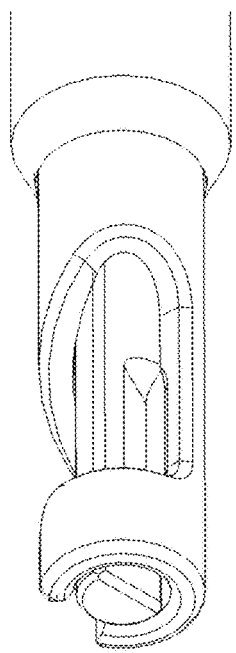
Figure 19E:
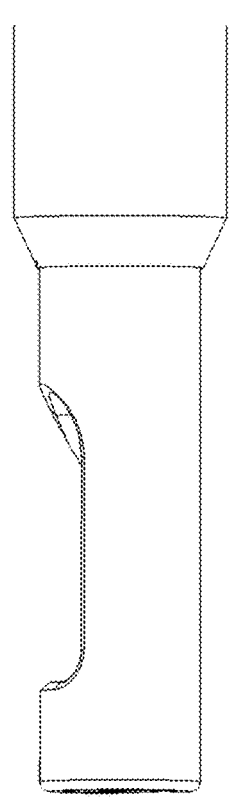
FIGS. 19E and 19F show bottom and bottom side views, respectively, of the distal end knot pusher and suture cutter shown in FIGS. 19A and 19B. The apparatus may be configured so that the mandrel is biased to remain in this position unless it is displaced by a control on the handle to rotate out of the way of a suture at the distal end, as shown.
Figure 19F:
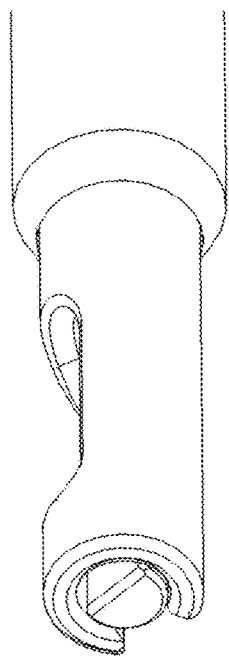

FIGS. 16A-16C and 17A-17C illustrate another variation of a knot pusher and cutter apparatus as described above. In this example, the handle includes a first control 1601 (e.g., a cutter control) and a second control 1603 (e.g., a mandrel control or inner mandrel control). These controls may be on the same side (e.g., top side) of the handle. In this example, both controls are slider; they may alternatively or additionally be dials, buttons, wheels, knobs, or the like. FIG. 16B illustrates actuation of the mandrel control (shown by arrow) to drive rotation of the inner mandrel (shown by curved arrow); alternatively or additionally the control may move the inner mandrel proximally.

As mentioned, in any of the variations described herein, the apparatus may be configured so that the rotation and/or axial motion of the inner mandrel is biased so that that mandrel is held in a configuration preventing a suture from entering or exiting the distal end of the device. A bias may be spring or other biasing element. In addition, the cutter may be biased by a second spring or other biasing element to hold it proximally until force is applied by the cutter control to push it distally to cut the suture, as illustrated above.

FIGS. 18A-18F illustrate another variation of a distal end region of a knot pusher and suture cutter apparatus, similar to that illustrated above. In this example the elongate holding tube 1805 is attached to the handle (not shown), and the elongate holding tube 1805 includes a lateral slot opening 1810 from a distal end of the holding tube extending proximally. The lateral slot extends in a somewhat P-shaped opening unlike the J- and L-shaped openings described above. The distal end opening of the lateral slot region is radially offset (e.g., between 30 and 90 degrees) from a proximal-most tip of the opening, which may help position the suture when loading and cutting. The lateral slot region is configured to allow a suture to pass therethrough when the inner mandrel 1807 is rotated out of the way, as shown in FIGS. 18A-18F. The lateral side opening (slot) curves around a central elongate axis of the elongate holding tube forming the opening 1810.

FIGS. 19A-19F illustrate the same views of FIGS. 18A-18F but with the inner mandrel 1907 rotated so that at least a portion of the inner mandrel 1907 covers the lateral opening 1810. This configuration may be the biased (preset) configuration of the inner mandrel, and may hold the length of suture within the distal end of the device, as described above.

Figure 20A:
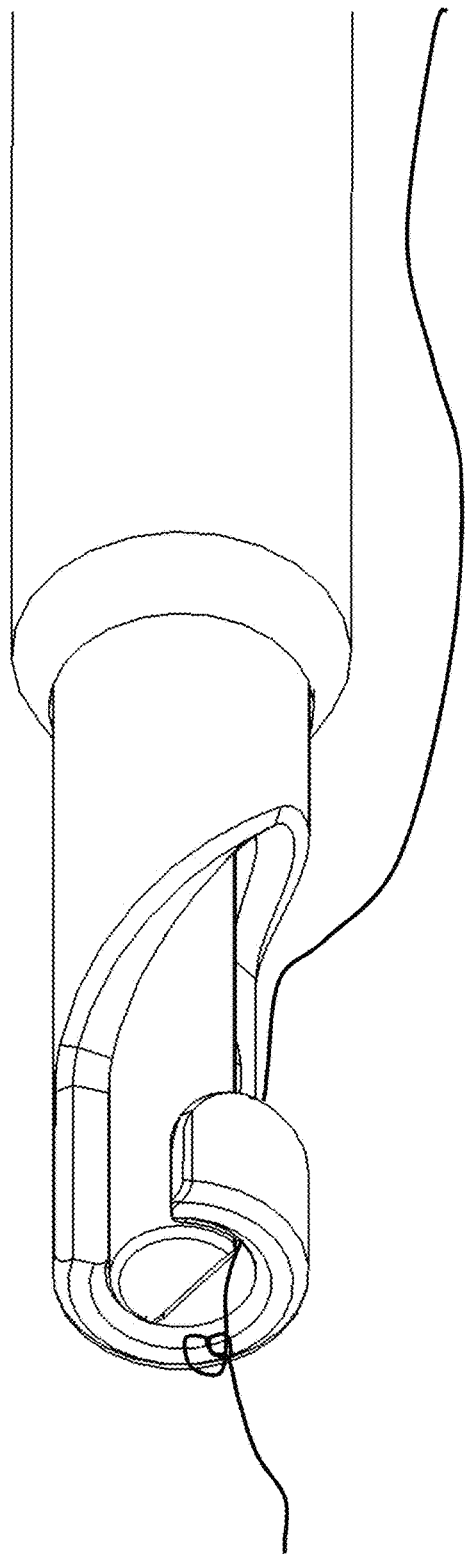
FIGS. 20A and 20B illustrate operation of a knot pusher and cutter apparatus as described herein. In this example a suture has been loaded into the distal end region as described above in reference to FIGS. 18A-18F by rotating the mandrel (e.g., mandrel control on the handle) to form an opening, and releasing the mandrel and/or rotating it back to lock the suture within the distal end, as shown in FIG. 20A. Thereafter, the cutting/cutter control on the proximal handle may by actuated to drive the cutting outer cannula distally and cut the knotted suture, as shown in FIG. 20B.
Figure 20B:
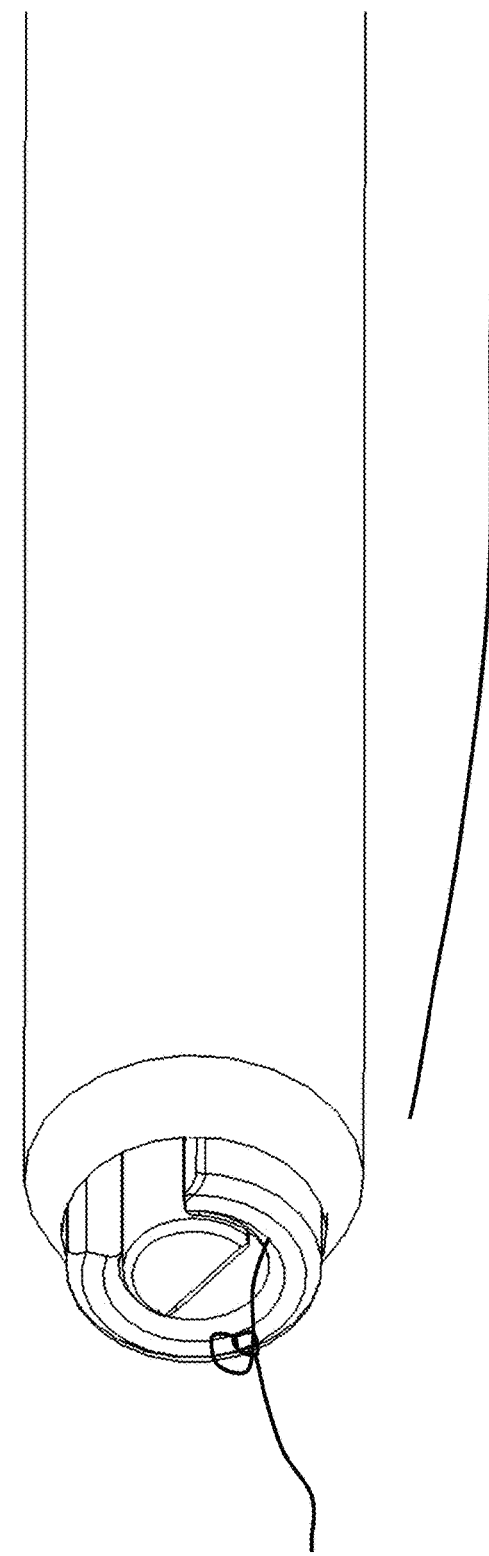

FIGS. 20A and 20B illustrate operation of the distal end configuration shown in FIGS. 18A-19F, similar to operation of the apparatuses already described above, in which the cutter control on the handle (not visible in FIG. 20A) is actuated against a bias force (e.g., spring) to drive the cutter distally to cut the suture, as shown in FIG. 20B.

Thus, for example, a surgical knot pusher and suture cutter apparatus may include: a handle; an elongate holding tube attached to the handle, the elongate holding tube including a lateral slot opening from a distal end of the holding tube and configured to allow a suture to pass therethrough, the lateral side opening curving around a central elongate axis of the elongate holding tube; an inner mandrel within the holding tube, the inner mandrel having a lateral notch extending proximally from a distal end of the inner mandrel, wherein the inner mandrel is axially or rotationally movable relative to the holding tube and is configured to capture the suture between the notch of the inner mandrel and the holding tube; a tubular cutter around the holding tube, the cutter configured to be axially movable relative to the holding tube to cut an end of the suture when the tubular cutter is extended distally; a cutter control on the handle configured to control the axial motion of the cutter; and a mandrel control on the handle, configured to control the rotational position of the inner mandrel within the elongate holding tube, wherein the mandrel control is biased such that the inner mandrel blocks at least a portion of the lateral slot until the mandrel control is actuated.

A surgical knot pusher and suture cutter apparatus may include: a handle; an elongate holding tube attached to the handle, the elongate holding tube including an open lateral slot through the distal end of the holding tube and configured to allow a suture to pass therethrough, the lateral slot extending from a distal end of the elongate tube and curving around a central elongate axis of the elongate holding tube as it extends proximally down the elongate holding tube; an inner mandrel within the holding tube, the inner mandrel having a lateral notch extending proximally from a distal end of the inner mandrel, wherein the inner mandrel is rotationally movable relative to the holding tube, the inner mandrel configured to capture the suture between the inner mandrel and the holding tube when the inner mandrel is held in a first rotational position; a tubular cutter extending around the holding tube, the cutter configured to be axially movable relative to the holding tube to cut an end of the suture; a mandrel control configured as a slider on the handle and configured to be operated with a single finger and to control the rotation of the inner mandrel; a cutter control on the handle configured to control the axial motion of the cutter; a first bias configured to hold the inner mandrel in the first rotational position until actuation of the mandrel control against the bias to rotate the mandrel control; and a second bias configured to oppose distal movement until force is applied on the cutter control to slide the cutter distally.

Alternatively or additionally, a surgical knot pusher and suture cutter apparatus may include: a handle; an elongate holding tube attached to the handle, the elongate holding tube including a lateral slot opening from a distal end of the holding tube and configured to allow a suture to pass therethrough; an inner mandrel within the holding tube, the inner mandrel having a notch extending proximally from a distal end of the inner mandrel along a side region of the inner mandrel, wherein the inner mandrel is axially or rotationally movable relative to the holding tube, wherein the inner mandrel is configured to capture the suture between the inner mandrel and the holding tube when the notch is rotated away from the lateral slot opening; a tubular cutter around the holding tube, the tubular cutter configured to be axially movable relative to the holding tube to cut an end of the suture when extended distally; a first control on the handle configured to control the axial motion of the cutter; a mandrel control on the handle configured to rotate the inner mandrel relative to the holding tube or to axially slide the inner mandrel proximally relative to the holding tube; and a thumb ring at the proximal end of the device.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of pushing a suture knot with a surgical knot pusher and suture cutter apparatus, the method comprising:
   sliding a control on a handle of the apparatus proximally to retract an inner member proximally;
   placing a suture into a lateral side opening of an elongate holding tube of the apparatus so that the suture extends from a distal end of the apparatus and also from the lateral side opening;
   advancing the inner member distally within the elongate holding tube to secure the suture between the inner member and the elongate holding tube;
   pushing a knot on the suture by advancing the apparatus distally over the suture;
   engaging a cutter release on the handle to permit a tubular cutter on the outside of the elongate holding tube to be advanced distally;
   sliding the control on the handle of the apparatus distally to advance the tubular cutter after engaging the cutter release; and
   cutting the suture using a distal-facing beveled edge of the tubular cutter.

2. The method of claim 1, wherein sliding the control on the handle of the apparatus proximally to retract the inner member proximally comprises sliding the control proximally with a single finger, wherein the control comprises a slider.

3. The method of claim 1, wherein sliding the control on the handle of the apparatus proximally to retract the inner member proximally comprises sliding the control proximally against a bias force operating to keep the inner member positioned distally.

4. The method of claim 1, wherein placing the suture into the lateral side opening further comprises hooking the suture into a generally J-shaped opening or L-shaped lateral side opening.

5. The method of claim 1, wherein advancing the inner member distally comprises releasing the control to permit the inner member to advance distally.

6. The method of claim 1, wherein advancing the inner member distally comprises sliding the control distally to advance the inner member distally.

7. The method of claim 1, wherein engaging the cutter release may comprises pushing on the cutter release with an index finger of a hand while a thumb of the hand operates the control on the handle.

8. The method of claim 1, wherein sliding the control on the handle of the apparatus distally comprises sliding a slider with a thumb while concurrently pushing on the cutter release with a finger.

9. The method of claim 1, wherein placing the suture into the lateral side opening comprises placing the suture into the lateral side opening so that a first length of the suture extends at one end distally from the apparatus and a second length of the suture extends from another end laterally from the lateral side opening.

10. The method of claim 1, further comprising loading the suture into the apparatus by first displacing the inner member to expose a continuous opening from the distal end and along a lateral slot and loading the suture into the opened lateral slot so that one end of the suture extends distally and a second end extends laterally.

11. The method of claim 1, further comprising displacing the inner member by axially sliding the inner member proximally or distally.

12. The method of claim 1, further comprising displacing the inner member by rotating the inner member so that a notch on a side of the inner mender is aligned with a lateral slot at the distal end of the apparatus.

13. The method of claim 1, further comprising locking a position of the inner member after placing the suture into the lateral side opening so that it cannot be accidentally moved.

14. A method of pushing a suture knot with a surgical knot pusher and suture cutter apparatus, the method comprising:
   placing a surgical knot pusher and cutter apparatus over a suture so that the suture passes through a lateral slot of an elongate holding tube of the apparatus, the lateral slot extending from a distal end of the elongate holding tube, wherein the holding tube extends from a handle;
   moving an inner mandrel within the holding tube to extend the inner mandrel distally within the elongate holding tube, the inner mandrel having a lateral notch extending proximally from a distal end of the inner mandrel along a side region of the inner mandrel, wherein extending the inner mandrel distally captures the suture between the notch of the inner mandrel and the holding tube;
   preventing axial movement of the inner mandrel until a lock out tab is released, wherein the lock out tab is coupled to the inner mandrel;
   pushing a knot on the suture by advancing the apparatus distally over the suture; and
   axially moving a tubular cutter relative to the holding tube, wherein the tubular cutter is positioned around the holding tube, to cut an end of the suture when the tubular cutter is extended distally;
   wherein the axial motion of both the inner mandrel and the cutter is controlled by a control on the handle.

15. The method of claim 14, further comprising releasing the surgical knot pusher and cutter apparatus from the suture by releasing a cutter release configured to prevent axial motion of the cutter.

16. The method of claim 14, wherein moving the inner mandrel comprises sliding the control on the handle of the apparatus proximally to retract the inner mandrel proximally with a single finger, wherein the control comprises a slider.

17. The method of claim 14, further comprising sliding the control on the handle of the apparatus proximally to retract the inner mandrel proximally against a bias force operating to keep the inner mandrel positioned distally before pacing the apparatus over the suture.

18. A method of pushing a suture knot and cutting suture, comprising:

passing a suture through a slot in an elongate holding tube into a suture receiving region defined by an inner mandrel, the inner mandrel having a D-shaped cross-section forming a notch extending proximally from a distal end of the inner mandrel along a side region of the inner mandrel, the notch defining the suture receiving region;

rotating the inner mandrel within the holding tube to move the notch out of alignment with the slot to secure the suture between the inner mandrel and the holding tube;

pushing a knot on the suture by advancing the holding tube distally over the suture;

advancing an outer tubular cutter over the holding tube; and cutting the suture using a distal-facing edge of the tubular cutter.

19. The method of claim 18 further comprising rotating the inner mandrel against a bias force to pass the suture through the slot.

* * * * *